(12) United States Patent
Sicotte et al.

(10) Patent No.: US 11,813,184 B2
(45) Date of Patent: Nov. 14, 2023

(54) SYSTEMS AND METHODS FOR IMPLANTS AND DEPLOYMENT DEVICES

(71) Applicant: ZENFLOW, INC., San Francisco, CA (US)

(72) Inventors: Marcel Song Sicotte, San Francisco, CA (US); Shreya Mehta, San Francisco, CA (US); Austin Michael Bly, San Clemente, CA (US); Ronald J. Jabba, Redwood City, CA (US)

(73) Assignee: ZENFLOW, INC., San Francisco, CA (US)

( * ) Notice: Subject to any disclaimer, the term of this patent is extended or adjusted under 35 U.S.C. 154(b) by 302 days.

(21) Appl. No.: 17/177,772

(22) Filed: Feb. 17, 2021

(65) Prior Publication Data

US 2021/0275335 A1    Sep. 9, 2021

Related U.S. Application Data

(60) Division of application No. 16/155,506, filed on Oct. 9, 2018, now Pat. No. 10,952,885, which is a
(Continued)

(51) Int. Cl.
*A61F 2/966* (2013.01)
*A61F 2/88* (2006.01)
(Continued)

(52) U.S. Cl.
CPC .............. *A61F 2/966* (2013.01); *A61F 2/885* (2013.01); *A61B 17/3468* (2013.01); *A61F 2/9517* (2020.05); *A61F 2002/048* (2013.01)

(58) Field of Classification Search
CPC ............. A61F 2/966; A61F 2/885; A61F 2/95
See application file for complete search history.

(56) References Cited

U.S. PATENT DOCUMENTS

| | | | |
|---|---|---|---|
| 4,813,925 A | 3/1989 | Anderson et al. | |
| 5,490,860 A | 2/1996 | Middle et al. | |
| (Continued) | | | |

FOREIGN PATENT DOCUMENTS

| | | | |
|---|---|---|---|
| CN | 101247777 A | 8/2008 | |
| CN | 102065794 A | 5/2011 | |
| (Continued) | | | |

OTHER PUBLICATIONS

CN, 201780024866.8 First Office Action, dated Apr. 14, 2020.
(Continued)

*Primary Examiner* — Suzette J Gherbi
(74) *Attorney, Agent, or Firm* — ONE LLP

(57) ABSTRACT

Benign prosthetic hyperplasia (BPH) is a non-cancerous enlargement of the prostate gland. Treatment options for BPH include medication, surgery (e.g., removal of enlarged prostate tissue), and minimally invasive procedures (e.g., needle ablation, electrovaporization, thermotherapy, and stent insertion). Minimally invasive procedure is typically the preferred choice if medication is ineffective. Accordingly, disclosed herein are system and method for treating BPH using improved implant and delivery device. Certain embodiments of the delivery device can include: a camming barrel having a first groove at the distal end of the camming barrel; a sheath, located within a lumen of the camming barrel, for storing the implantable device; and a first cam follower coupled to the sheath.

14 Claims, 27 Drawing Sheets

Related U.S. Application Data continuation of application No. PCT/US2017/028677, filed on Apr. 20, 2017.

(60) Provisional application No. 62/325,939, filed on Apr. 21, 2016.

(51) Int. Cl.
  *A61B 17/34* (2006.01)
  *A61F 2/04* (2013.01)
  *A61F 2/95* (2013.01)

(56) References Cited

U.S. PATENT DOCUMENTS

| | | | |
|---|---|---|---|
| 5,830,228 A | 11/1998 | Knapp et al. | |
| 7,192,440 B2 | 3/2007 | Andreas et al. | |
| 8,708,953 B2 | 4/2014 | Salahieh et al. | |
| 10,952,885 B2 * | 3/2021 | Sicotte | A61F 2/966 |
| 11,571,215 B2 * | 2/2023 | Shelton, IV | A61B 17/00491 |
| 2005/0137716 A1 | 6/2005 | Gross | |
| 2006/0276909 A1 | 12/2006 | Gellman | |
| 2008/0015633 A1 | 1/2008 | Abbott et al. | |
| 2008/0249466 A1 * | 10/2008 | Aubert | A61M 31/007 604/117 |
| 2011/0093007 A1 | 4/2011 | Abbott et al. | |
| 2013/0006048 A1 * | 1/2013 | Fisher | A61B 17/3468 600/37 |
| 2014/0288627 A1 | 9/2014 | Ouellette et al. | |
| 2015/0257908 A1 * | 9/2015 | Chao | A61F 2/86 623/23.66 |
| 2016/0262862 A1 * | 9/2016 | Fischer | A61B 17/06109 |
| 2017/0065406 A1 * | 3/2017 | Calomeni | A61F 2/2436 |
| 2017/0333042 A1 * | 11/2017 | Sato | A61B 17/00234 |
| 2019/0038443 A1 | 2/2019 | Sicotte et al. | |
| 2019/0117423 A1 | 4/2019 | Chao et al. | |
| 2019/0307548 A1 | 10/2019 | Sicotte et al. | |
| 2020/0038213 A1 | 2/2020 | Bly et al. | |
| 2020/0146823 A1 * | 5/2020 | Alon | A61F 2/2418 |
| 2020/0323618 A1 | 10/2020 | Bly et al. | |
| 2021/0038885 A1 * | 2/2021 | Grace | A61B 17/32053 |
| 2021/0275335 A1 * | 9/2021 | Sicotte | A61F 2/966 |
| 2022/0015792 A1 * | 1/2022 | Grace | A61B 17/50 |
| 2022/0039970 A1 * | 2/2022 | Elliot | A61B 17/1675 |
| 2022/0257225 A1 * | 8/2022 | Grant | A61B 17/0057 |

FOREIGN PATENT DOCUMENTS

| | | |
|---|---|---|
| CN | 104470471 A | 3/2015 |
| EP | 1321111 A2 | 6/2003 |
| EP | 2839872 A1 | 2/2015 |
| WO | WO 96/26682 A1 | 9/1996 |
| WO | WO 2007/005799 A1 | 1/2007 |
| WO | WO 2011/102968 A1 | 8/2011 |
| WO | WO 2012/036741 A2 | 3/2012 |
| WO | WO 2016/022899 A1 | 2/2016 |

OTHER PUBLICATIONS

EP, 17786650.6 Supplementary Search Report, dated Nov. 21, 2019.
WO, PCT/US2017/028677 ISR and Written Opinion, dated Aug. 14, 2017.

* cited by examiner

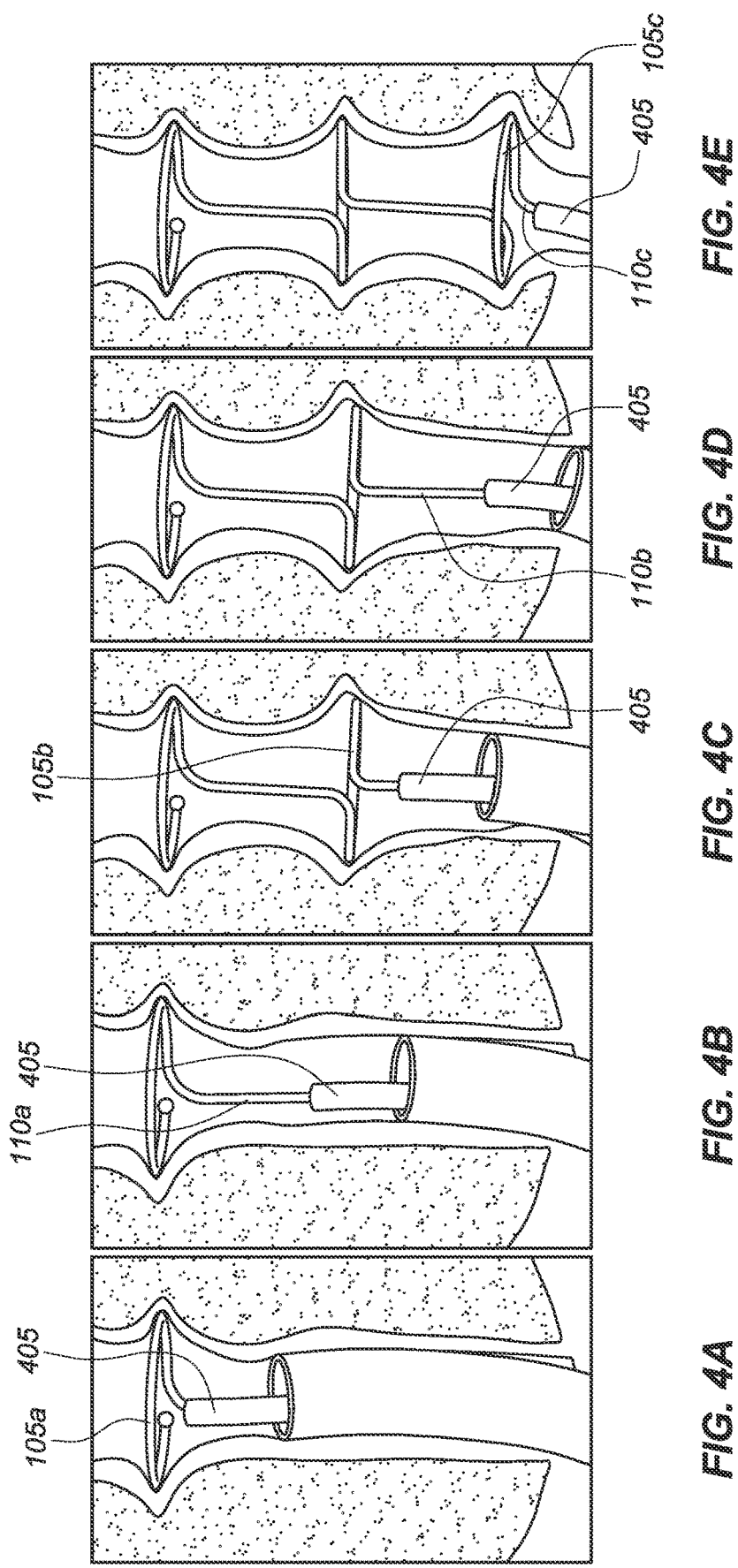

SYSTEMS AND METHODS FOR IMPLANTS AND DEPLOYMENT DEVICES

CROSS-REFERENCE TO RELATED APPLICATION

This application is a divisional of U.S. application Ser. No. 16/155,506, filed Oct. 9, 2018, which is a continuation of PCT Application No. PCT/US17/28677, filed Apr. 20, 2017, which claims the benefit of and priority to U.S. Provisional Application No. 62/325,939, filed Apr. 21, 2016, all of which are incorporated by reference herein in their entireties for all purposes.

STATEMENT OF GOVERNMENT SPONSOR RESEARCH

This invention was made with government support under SBIR Phase I Award #1520412 and Phase D3 Award #1602731, both awarded by National Science Foundation. The government has certain rights in the invention.

FIELD

Various aspects of the disclosure relate to a system and method for implants and deployment devices.

BACKGROUND

Benign prosthetic hyperplasia (BPH), also known as benign prostatic hypertrophy, is a non-cancerous enlargement of the prostate gland. BPH is a condition that mainly occurs in older men. Treatment options for BPH include medication, surgery (e.g., removal of enlarged prostate tissue), and minimally invasive procedures (e.g., needle ablation, electrovaporization, thermotherapy, and stent insertion). Currently, most patients opt for surgical treatment if medication is ineffective. However, minimally invasive procedures are becoming increasingly popular and common. Accordingly, disclosed herein are systems and methods for treating BPH using improved implants and deployment devices.

SUMMARY

Example embodiments of delivery devices and systems are disclosed, as are example embodiments of components of the systems and methods of using the systems and/or components thereof. Certain embodiments of the delivery device can include: a camming barrel having a first groove at the distal end of the camming barrel; a sheath, located within a lumen of the camming barrel, for storing the implantable device; and a first cam follower coupled to the sheath. In some embodiments, the first cam follower is configured to travel within the first groove of the camming barrel and to translate the sheath, which causes the sheath to retract into the camming barrel.

In some embodiments, the camming barrel can include a second groove that is designed to translate a second cam follower coupled to a pusher shaft. The translation of the second cam follower causes the pusher shaft to be pushed in the distal direction to assist in deploying the implantable device attached to the distal end of the pusher shaft. The first groove can be disposed near the distal end of the camming barrel, and the second groove can be disposed near the proximal end of the camming barrel. In some embodiments, each of the grooves can be formed by a plurality of linked helical and/or radial slots. In some embodiments, the first and second grooves can be arranged such that the first cam follower is traversing a helical slot of the first groove while the second cam follower of the second groove is concurrently or simultaneously traversing a radial slot of the second groove. In this way, the movements of both cam followers are not required to be the same at every point of time. This enables two main types of coordinated movement of the cam followers. The first type of coordinated movement is when the first cam follower retracts the sheath in the proximal direction while the second cam follower holds the pusher shaft axially stationary. The second type of coordinated movement is when the first cam follower holds the sheath axially stationary while the second cam follower pushes the pusher shaft forward in the distal direction.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The foregoing summary, as well as the following detailed description, is better understood when read in conjunction with the accompanying drawings. The accompanying drawings, which are incorporated herein and form part of the specification, illustrate a plurality of embodiments and, together with the description, further serve to explain the principles involved and to enable a person skilled in the relevant art(s) to make and use the disclosed technologies.

FIGS. 4A-4E depict an example deployment procedure of an implantable device in accordance with some embodiments of the disclosure.

DETAILED DESCRIPTION

Overview

Figure 1:
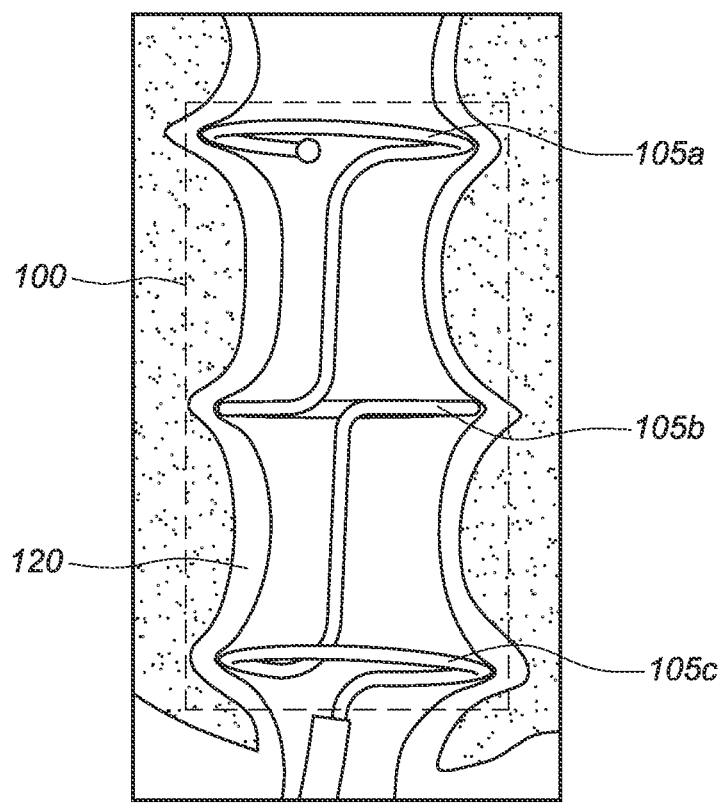
FIG. 1 depicts an example embodiment of an implantable device being deployed within a urethra.

As previously mentioned, treatment options for BPH-related urinary obstruction include medication and surgery. However, both treatment options have many adverse side effects and risks. An alternative treatment for BPH symptoms with fewer risks and side effects is to use an implantable device that mechanically holds open the urethra. FIG. 1 illustrates an implantable device 100 implanted within the urethra in accordance with some embodiments of the disclosure. In some embodiments, implantable device 100 can be a partially helical structure and can have two or more ring members (e.g., ring members 105a, 105b, and 105c) and one or more connecting members (e.g. 110a and 110b). As shown, ring members 105a, 105b, and 105c of implantable device 100 maintain urethra 120 in an open state. Device 100 can be manufactured in various sizes as desired, such that the radius of each ring member 105 determines the size of the opening, and the length of each connecting member 110 determines the spacing between the ring members 105.

Implantable device 100 can be deployed into urethra 120 using a delivery device (described below) that can rotate implantable device 100 with respect to a delivery sheath and concurrently expose it from within the delivery device. In this way, the wall of the urethra is not irritated by an abrupt pushing or scraping motion of the implantable device. The gentle spinning deployment of implantable device 100 can also reduce the risk of tearing or rupturing the wall of the urethra. In other embodiments, device 100 can be deployed without rotating it with respect to the delivery device. Once implantable device 100 is in place within urethra 120, the delivery device can release implantable device 100. Depending upon the patient's condition and urethra anatomy, one or more implantable devices 100 or a different size (e.g., larger radius, longer axial length) implantable device 100 can be implanted into urethra 120.

Implantable Device

Figure 2:
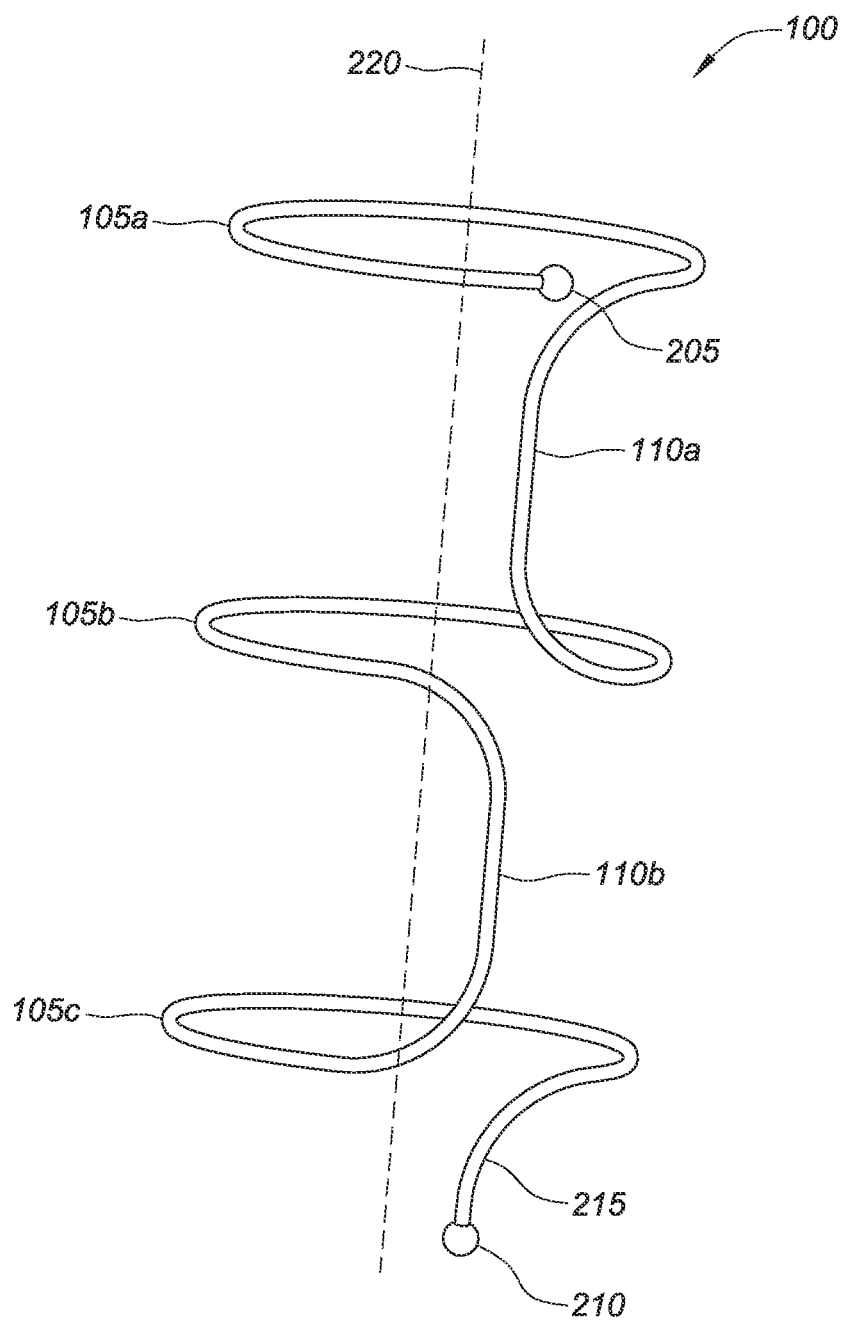
FIGS. 2-3 are perspective views depicting example embodiments of implantable devices.

FIG. 2 illustrates an implantable device 100 in accordance with some example embodiments of the present disclosure. In this instance, implantable device 100 includes three ring members 105a, 105b, and 105c, and two connecting members 110a and 110b to form a bracing or scaffold-like structure. Connecting member 110a bridges between ring members 105a and 105b and connecting member 110b bridges between ring members 105b and 105c. To increase the ring member density of implantable device 100, additional rings 105 can be added and at the same the length of the connecting members 110 can be shortened to maintain the same overall length. Implantable device 100 also includes a termination member 215, which connects the last ring member (e.g., 105c) to end member 210.

Each of the connecting members 110 can be substantially parallel to a center axis 220, which can be a common axis to each of the ring members 105. In other words, each of the connecting members 110a and 110b is substantially perpendicular to the planes of the ring members 105. In this embodiment, the plane of each ring member 105 is substantially parallel to the plane of other ring members 105 and is substantially perpendicular to common axis 220. In some embodiments, the plane of each ring member 105 can be angled with respect to common axis 200. Each connecting member 110 can also be angled with respect to common axis 200 rather than being parallel. Connecting members 110a and 110b do not have to be equal in length. For example, connecting member 110a can be a first length (e.g., 6 mm) and member 110b can be a second length (e.g., 7 mm). Ring spacing can be adjusted to improve stability, performance, and tissue support. As already stated, implantable device 100 can have two or more ring members 105 and one or more connecting members 110, in alternating fashion, without departing from the scope of this disclosure.

In some embodiments, each ring member 105 is wound about axis 220 in an opposite direction of the winding direction of an adjacent ring member 105. For example, ring member 105a is wound in a first (e.g., clockwise) direction and the next ring member 105b is wound in a second opposite (e.g., counterclockwise) direction. Finally, the last ring member 105c is wound in the first direction. In some embodiments, all ring members 105 are wound in the same direction, clockwise or counterclockwise.

Implantable device 100 can also include a distal end member 205 and a proximal end member 210. Each of members 205 and 210 can be an enlarged atraumatic shape such as rounded enlarged shape like a partial sphere, which serves two main functions. First, an atraumatic shape provides a smooth and non-abrasive contact surface with the urethra wall. During deployment of implantable device 100, member 205 may rub against the urethra wall as implantable device 100 is being deployed. Thus, an atraumatic shape decreases the friction with the wall of urethra 120. When the surface area of member 205 or 210 is larger and preferably rounded, it is less traumatic to the tissue as it distributes forces across a larger surface area. Also, an enlarged shape can provide a surface for a grasping component to hold implantable device 100. The grasping component can have a circular slot designed to engage and lock spherical member 205 or 210 in place. The grasping component can be disposed at the distal end of the shaft (to be discussed later) of the delivery device.

Figure 3:
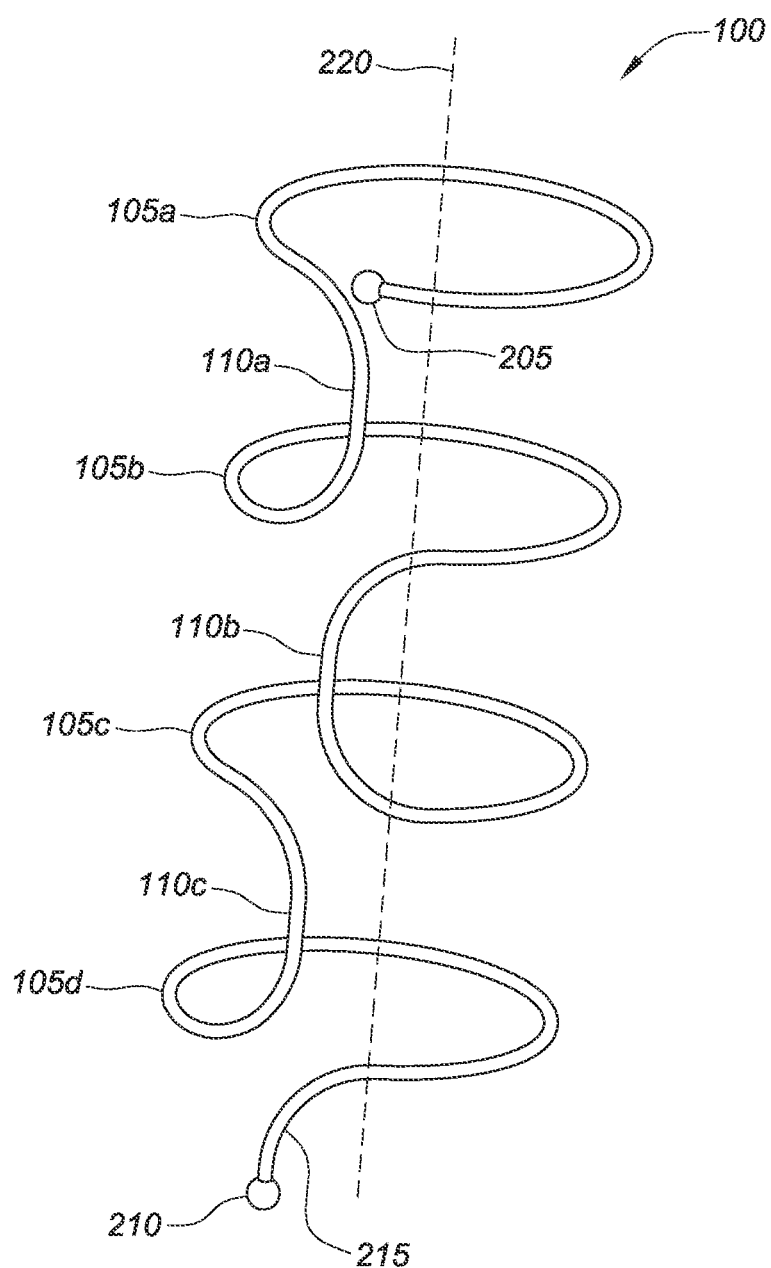

FIG. 3 illustrates an implantable device 100 in accordance with some embodiments of the present disclosure. In this embodiment, implantable device 100 includes four ring members 105a, 105b, 105c, and 105d. Each ring member 105 is separated by a connecting member (e.g., member 110a, 110b, or 110c). Each ring member 105 has an opposite winding direction as compared to the one or two adjacent ring members 105. For example, ring member 105a has a counterclockwise winding direction, ring member 105b has a clockwise winding direction, and ring member 105c has a counterclockwise winding direction. Each ring member 305 can have a common axis 220 and can be in a plane parallel to all other ring members 105.

Each of the connecting members 110a, 110b and 110c can be parallel to axis 220 or substantially normal to the plane of a ring member 105. Alternatively, each connecting member 110 can have angled (an angle other than 90 degree) with respect to the plane of the ring member 105 or axis 320.

FIGS. 4A-4E illustrate a process of deploying implantable device 100 into the urethra in accordance with some embodiments of the present disclosure. The process of deploying implantable device 100 can start by spiraling or spinning out ring member 105a as shown in FIG. 4A. Next, connecting member 110a is exposed by retracting sheath 405 (FIG. 4B) with respect to device 100, then second ring member 105b can be deployed by further rotating the shaft (not shown) connected to implantable device 100 (FIG. 4C). In FIG. 4D, the second connecting member 110b can be exposed by again retracting sheath 405. Finally, the last ring member 105c can be spiraled or spun out. Once implantable device 100 is in position, the delivery device can release implantable device by retracting sheath 405 to expose the opening of the grasping component located at the distal end of the shaft.

In other embodiments, sequential exposure of device 100 from within sheath 405 can occur by advancing device 100 with respect to sheath 405 as opposed to withdrawing sheath 405 as device 100 is held in a static position. In still other embodiments, exposure can occur by a combination of the two motions, where device 100 is moved distally while sheath 405 is retracted proximally. In some embodiments, connecting members 110a, 110b, and 110c can have variable lengths. In this way, the distance between any two ring members can be varied.

Figure 4F:
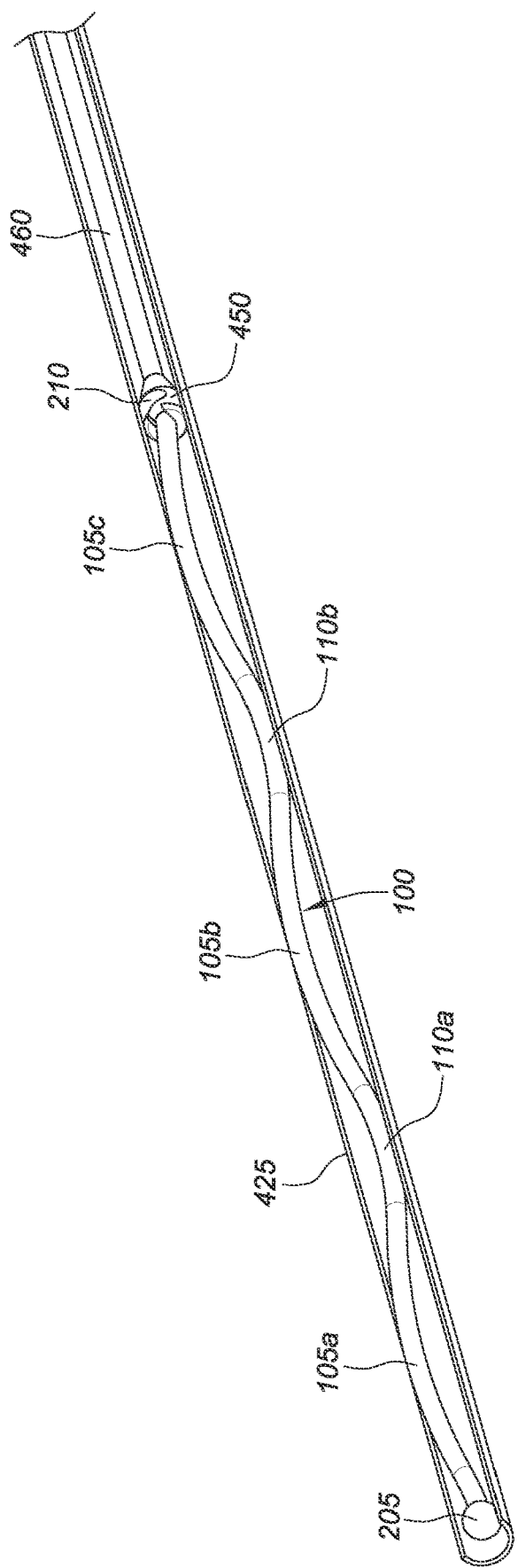
FIG. 4F is a perspective view depicting an example embodiment of an implantable device contained within a sheath and attached to a pusher shaft.

FIG. 4F illustrates implantable device 100 being housed within a distal region of sheath 425 prior to being deployed in accordance with some embodiments of the present disclosure. Sheath 425 can have radial openings (e.g., formed by cuts) to improve flexibility and/or deliverability. In some embodiments, a grasper 450 is provided at the end of a shaft 460. Grasper 450 can include a slot having a shape complementary to the atraumatic end 210 of implantable device 100. When shaft 460 is rotated and translated, grasper 450 also rotates and translates, which in turn rotates and pushes implantable device 100 out of sheath 425. In other words, the combination of rotations and translations of shaft 460 cause corresponding rotations and translations of implantable device 100, which cause implantable device 100 to gently spiral (or spin) out of sheath 425 and into the patient's urethra. When the atraumatic end 210 of device 100, in the coupled state with grasper 450, is exposed to the exterior from within the inner lumen of sheath 425, end 210 and grasper 450 are freed from the restraint imparted by sheath 425 and no longer held in the coupled state, at which point end 210 detaches from a pocket 475 of grasper 450 (see also FIG. 4G).

Figure 4G:
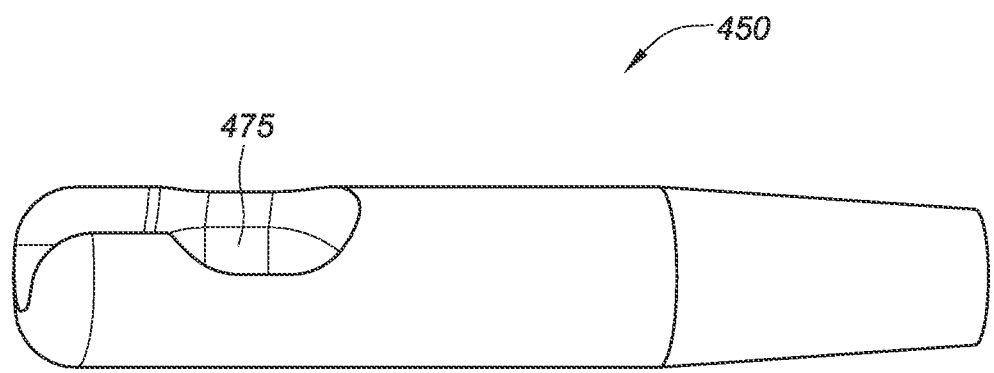
FIGS. 4G and 4H are perspective views depicting example embodiments of a grasper.
Figure 4H:
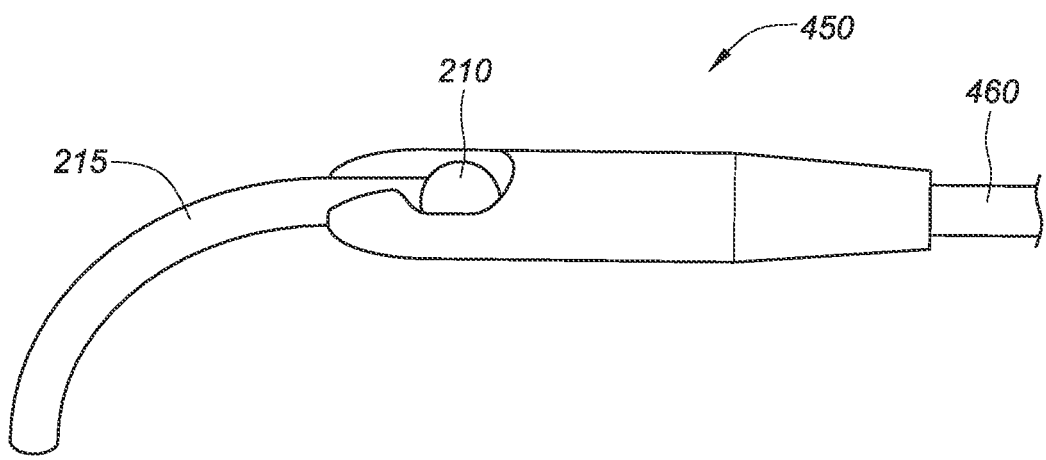

FIGS. 4G and 4H illustrate example embodiments of grasper 450 in accordance with some embodiments of the present disclosure. As shown in FIG. 4G, grasper 450 includes a cavity/pocket 475 for holding the end portion (e.g., atraumatic member 210) of implantable device 100. FIG. 4H shows implantable device 100 being attached to grasper 450. When implantable device is not within sheath 425, atraumatic member 210 can be released from (e.g., move out of) pocket 475 because it is no longer being constrained by the inner wall of sheath 425. Thus, once sheath 425 is retracted, implantable device is released.

Delivery/Retrieval Device

Figure 5A:
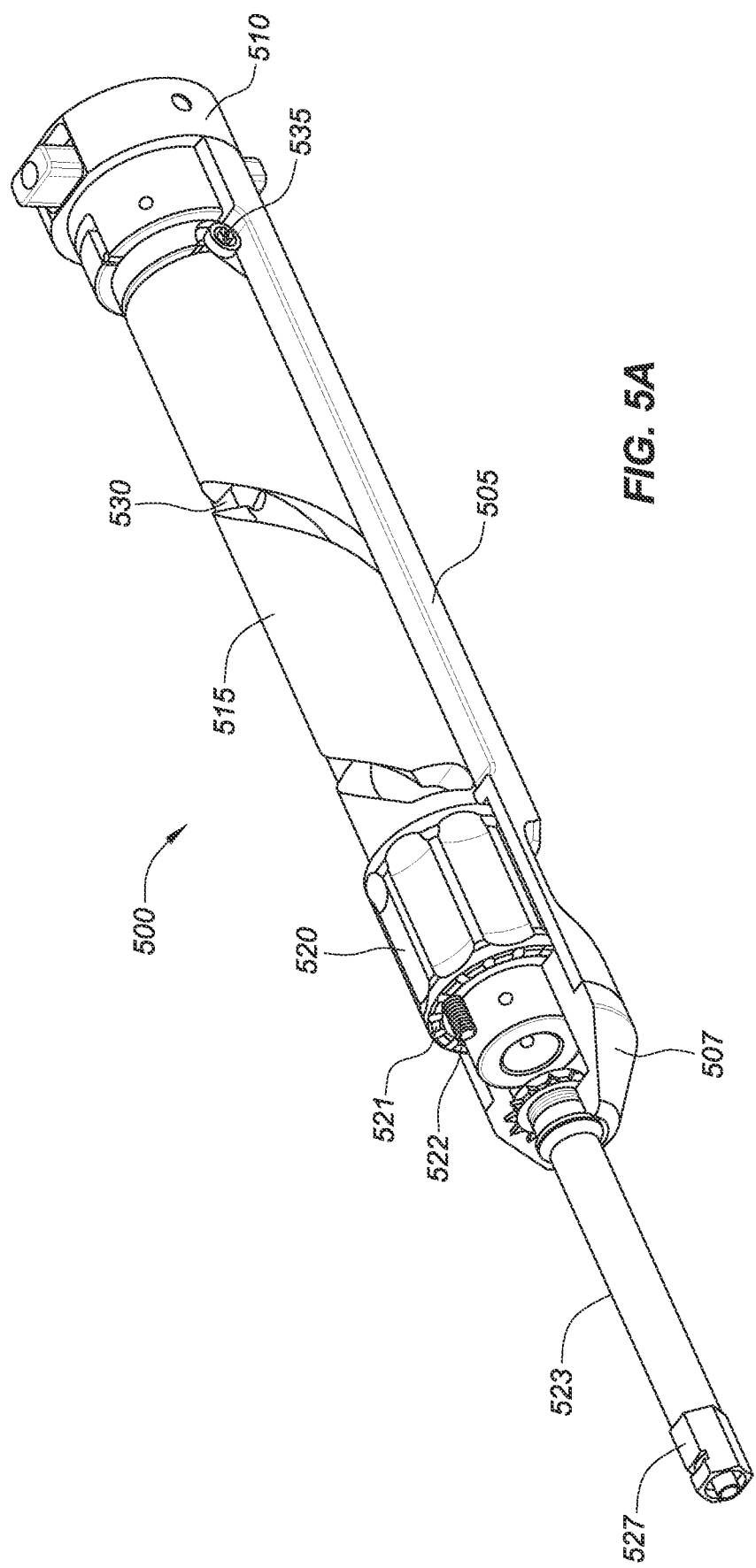
FIG. 5A is a perspective view depicting a delivery device in accordance with some example embodiments of the present disclosure.

FIG. 5A illustrates a delivery device 500 in accordance with some embodiments of the present disclosure. Delivery device 500 includes a main body 505, a front cap 507, and an end cap 510. Each of the main body 505, front cap 507, and end cap 510 has an internal cavity to contain and enclose a camming barrel 515 and a knob 520. Main body 505 can have an open substantially cylindrical shape such as a hollow tube. Front cap 507 can have a beveled surface with a narrow opening to enclose and secure an adapter shaft 523, which also can have a hollow inner portion to receive and contain a constraining sheath 425 (not shown, see FIG. 13). Adapter shaft 523 can also include a male luer fitting 527 to enable the attachment of various devices (e.g., a cystoscope) to adapter shaft 523.

Figure 5B:
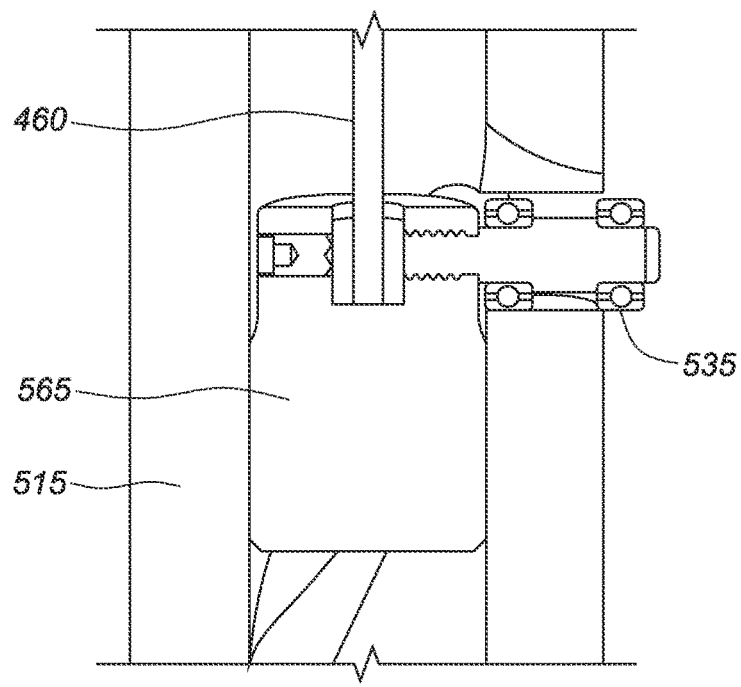
FIG. 5B is cross-sectional view depicting a portion of a delivery device in accordance with some example embodiments of the present disclosure.
Figure 5C:
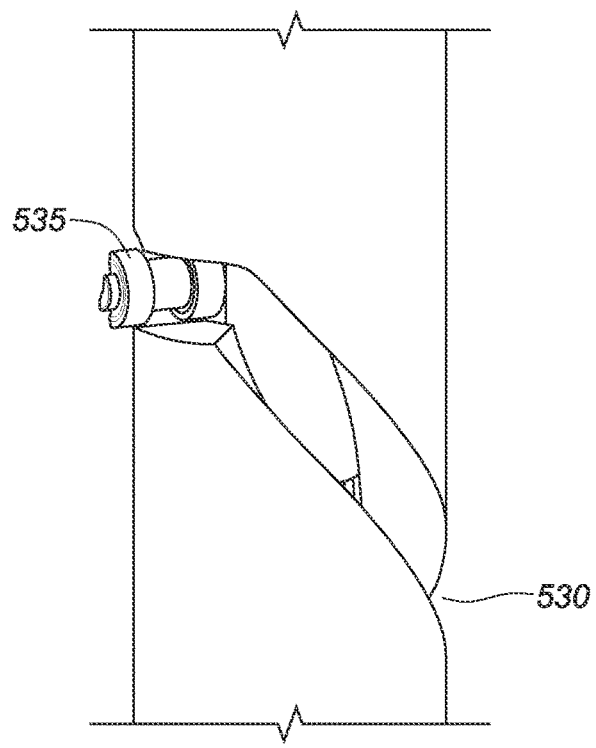
FIGS. 5C and 6A are perspective views depicting a delivery device in accordance with some example embodiments of the present disclosure.

Camming barrel 515 can include a groove 530 on the surface of camming barrel 515. Groove 530 can be completely cut through the wall of camming barrel 515 to allow a cam follower 535 to fit through groove 530. Cam follower 535 can be securely (or rigidly) coupled to a shaft-driver body (not shown, see FIG. 5B), which is also securely coupled to shaft 460 of delivery device 500 (not shown, see FIG. 7A). FIG. 5B illustrates an example embodiment cam follower 535 being coupled to shaft-driver body 565. FIG. 5B also shows shaft 460 being rigidly coupled to shaft-driver body 565. FIG. 5C is a close-up view of cam follower 535 disposed in groove 530. Each cam follower 535 or 550 can have a T-shaped or I-shaped cross-section with the flange portion extending through and out of the respective anti-rotation slot (e.g., slot 537 or slot 560). Cam followers 535 and 550 can have other shapes such as a cylinder for example, while remaining within the scope of this disclosure.

Knob 520 is rotatably secured by main body 505 and is fixedly attached to camming barrel 515. In some embodiments, knob 520 can be fixedly attached to camming barrel 515, e.g., with a pin, such that if knob 520 is rotated within main body 505, camming barrel 515 will also rotate along with knob 520. For example, if knob 520 is rotated counterclockwise, camming barrel 515 will also rotate counterclockwise. Knob 520 can include indentations 521 (see also FIG. 7B) on the on the front surface that interact with a plunger 522 affixed to front cap 507 to provide audible clicks and haptic feedback to the user that the knob is successfully turning.

Figure 6A:
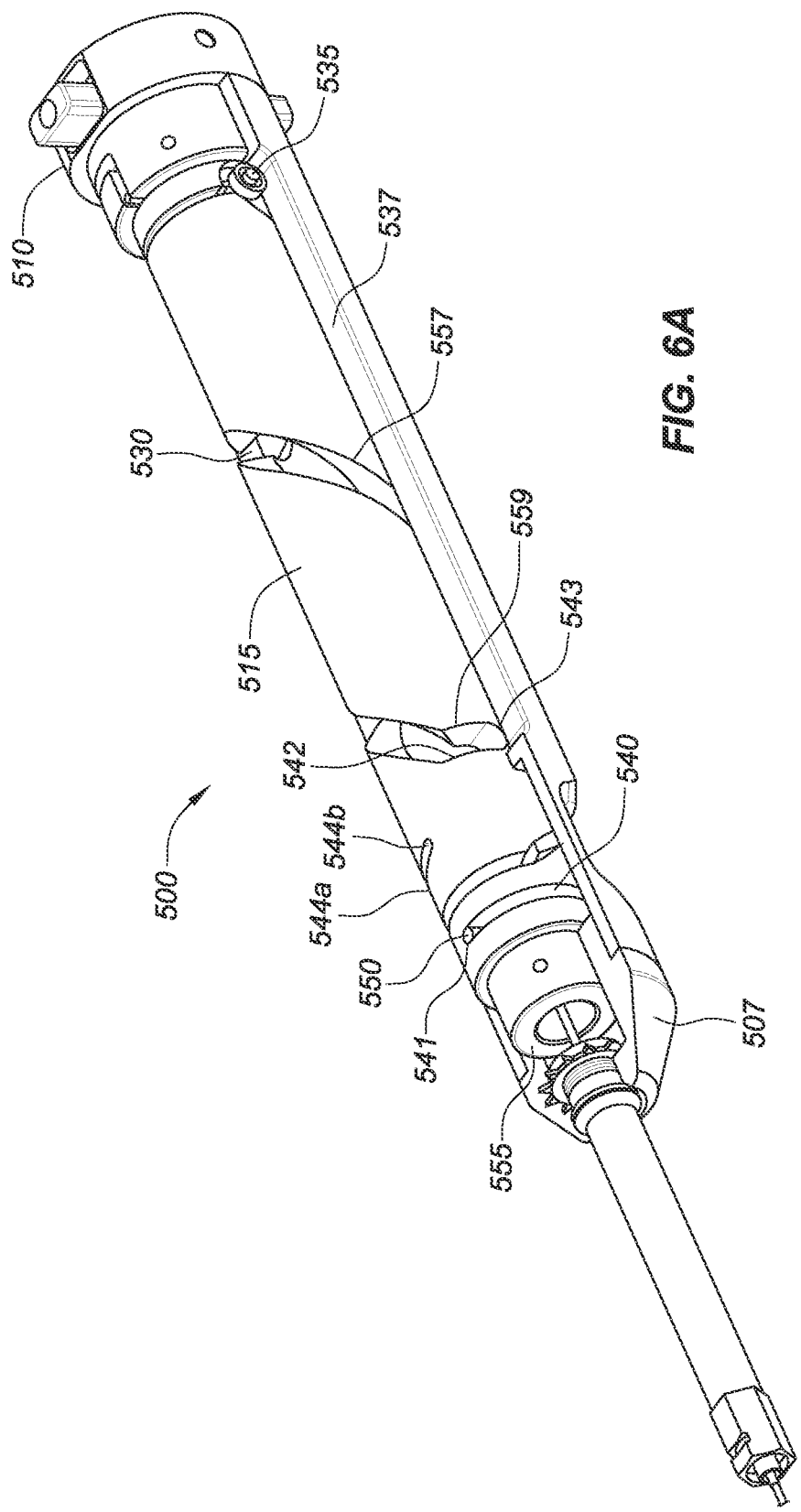

FIG. 6A illustrates delivery device 500 with knob 520 removed. In some embodiments, camming barrel 515 includes a second groove 540 located at the distal end of camming barrel 515. Delivery device 500 also includes a second cam follower (e.g. a nut, pin, etc.) 550, which travels within groove 540 when camming barrel 515 is rotated. As shown in FIG. 6A, cam followers 535 and 550 are both in their respective starting position. Grooves 530 and 540 (and groove 1105 described later) can also be described as slots or paths. The shapes of grooves 530, 540, and 1105 can and will vary depending upon the particulars of the implementation. In some embodiments, the shapes of grooves 530, 540, and 1105 can be described as forming a partially helical path.

Cam follower 535 starts at the proximal end (near end cap 510) of camming barrel 515 and ends at the distal end (near front cap 507) of camming barrel 515 at 543. In some embodiments, there are two end positions for cam follower 535. Position 542 is the penultimate position and position 543 is the very last position at the end of groove 530. The groove between penultimate position 542 and end position 543 is a radial slot 559 designed to allow camming barrel 515 to rotate but without any axial translation of shaft 460 (not shown, see FIG. 7A) or cam follower 535.

In an initial setting of delivery device 500, cam follower 535 can be set to stop at penultimate position 542 such that it cannot move beyond position 542 without requiring the user to unlock camming barrel 515. The locking mechanism that prevents cam follower 535 from moving from penultimate position 542 to end position 543 will be described in detail below.

As shown, cam follower 550 starts at position 541 and moves to penultimate position 544a as camming barrel 515 rotates. Once at penultimate position 544a, camming barrel 515 is rotationally locked by default to prevent cam follower 550 to move to end position 544b. Similar to cam follower 535, cam follower 550 cannot move to end position 544b without requiring the user to unlock the locking mechanism at the proximal end of camming barrel 515. This is to prevent the accidental release of implantable device 100 through the retraction of sheath 425.

In some embodiments, groove 530 can include multiple sloped (in some cases helical) and radial slots (e.g., slots 557 and 559 respectively), as well as other shapes, which can be linked together to form the desired path (which in turns imparts desired movements to the components). In the present description, certain sloped slots will be described as helical, although the term helical is used broadly herein and does not require a constant nor continuous slope. Indeed, these sloped slots can vary such that the slope reverses from positive to negative (like a "V") if desired.

Groove 530 can have three or more helical slots and radial slots. A sloped slot can be an opening in camming barrel 515 with an angle that moves the slot along the longitudinal axis of camming barrel 515 during rotation. A radial slot can include an opening perpendicular to the longitudinal axis of camming barrel 515 such that the cam follower moves in the slot but is not translated in the longitudinal direction.

Figure 6B:
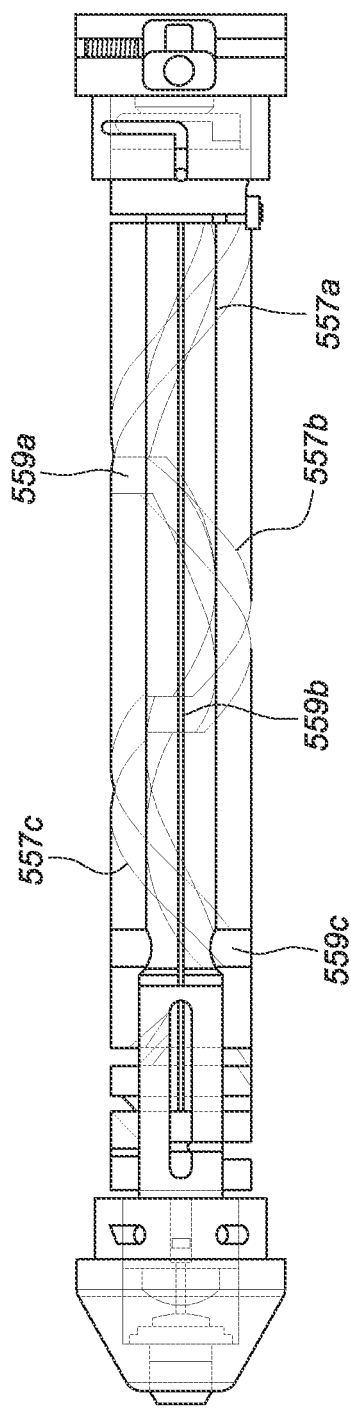
FIG. 6B is a side view depicting an example embodiment of delivery device.

In some embodiments, the number of helical slots on camming barrel 515 can correspond to the number of ring members 105 in implantable device 100. Similarly, the number of radial slots on camming barrel 515 can correspond to the number of connecting members 110 in implantable device 100 plus a termination member (e.g., member 215). For example, as shown in FIG. 2, implantable device 100 has three ring members (i.e., 105a, 105b, and 105c), two connecting members (i.e., 110a and 110b), and termination member 215. Accordingly, groove 530 has three helical slots 557a, 557b, 557c and three radial slots 559a, 559b, 559c (see FIG. 6B). Here, each radial slot 559 is perpendicular to the longitudinal axis of camming barrel 515. Thus, it can only rotate cam follower 535 about the longitudinal axis of camming barrel 515 and does not cause any translation of cam follower 535 and/or shaft 460. Radial slot 559 can also be described as a non-sloped slot. Since each helical slot 557 has an axial translation component, it forces cam follower 535 (and shaft-driver body 565) to translate in the axial direction as camming barrel 515 rotates.

Cam follower 535 is configured to travel within groove 530 while staying within a longitudinal slot 537 on main body 505. Longitudinal slot 537 (see also FIG. 14) constrains cam follower 535 to only move in the axial direction by preventing cam follower 535 to rotate along with camming barrel 515. In this way, cam follower 535 is forced to translate along the longitudinal axis of camming barrel 515 by slot 537.

In some embodiments, groove 540 is formed by chaining together a plurality of radial and helical slots. Grooves 530 and 540 can be arranged on camming barrel 515 such that when cam follower 535 is traversing a helical slot of groove 530, cam follower 550 is concurrently traversing a radial slot of groove 540. Similarly, while cam follower 535 is traversing a radial slot of groove 530, cam follower 550 is concurrently traversing a helical slot of groove 540.

Stated differently, there are at least two main types of coordinated movement between cam followers 535 and 550. The first type of coordinated movement is when cam follower 535 is traversing a helical slot of groove 530 while cam follower 550 is concurrently traversing a radial slot of groove 540. During the first coordinated movement, cam follower 535 and shaft 460 are being axially translated while cam follower 550 is concurrently traversing a radial slot (no axial movement). This causes the sheath-driver body (see item 570 of FIG. 7A) to rotate about its own axis (or the longitudinal axis of camming barrel 515) without any axial movement. In terms of the deployment, a portion of implantable device 100 is advanced out of sheath 425 during this stage, while sheath 425 remains stationary because there is no axial movement of the sheath-driver body.

Figure 10B:
FIGS. 10A-10N are side views depicting an example embodiment of a deployment procedure and the progression of the deployment.

The second type of coordinated movement involves cam follower 535 traversing a radial slot of groove 530 while cam follower 550 is concurrently traversing a helical slot of groove 540. During the second type of coordinated movement, cam follower 550 axially moves toward the proximal end of main body 550 while cam follower 535 remains axially stationary. The axial movement of cam follower 550 is caused by the rotation helical slot of groove 530, which pushes cam follower 550 along a slot in anti-rotation sleeve 555. The slot in anti-rotation sleeve 555 is parallel to the longitudinal axis of barrel 515. (This slot in sleeve 555 is illustrated in FIG. 10A as item 650.) The effect of this motion is the retraction of sheath 425 into the lumen of camming barrel 515.

In some embodiments, cam followers 535 and 550 can move independently of each other. In other words, each of cam followers 535 and 550 may be coupled to a separate and discrete cam. In this way, cam follower 535 can be moved in the distal direction while cam follower 550 can concurrently be moved in the proximal direction instead of staying axially stationary.

Figure 7A:
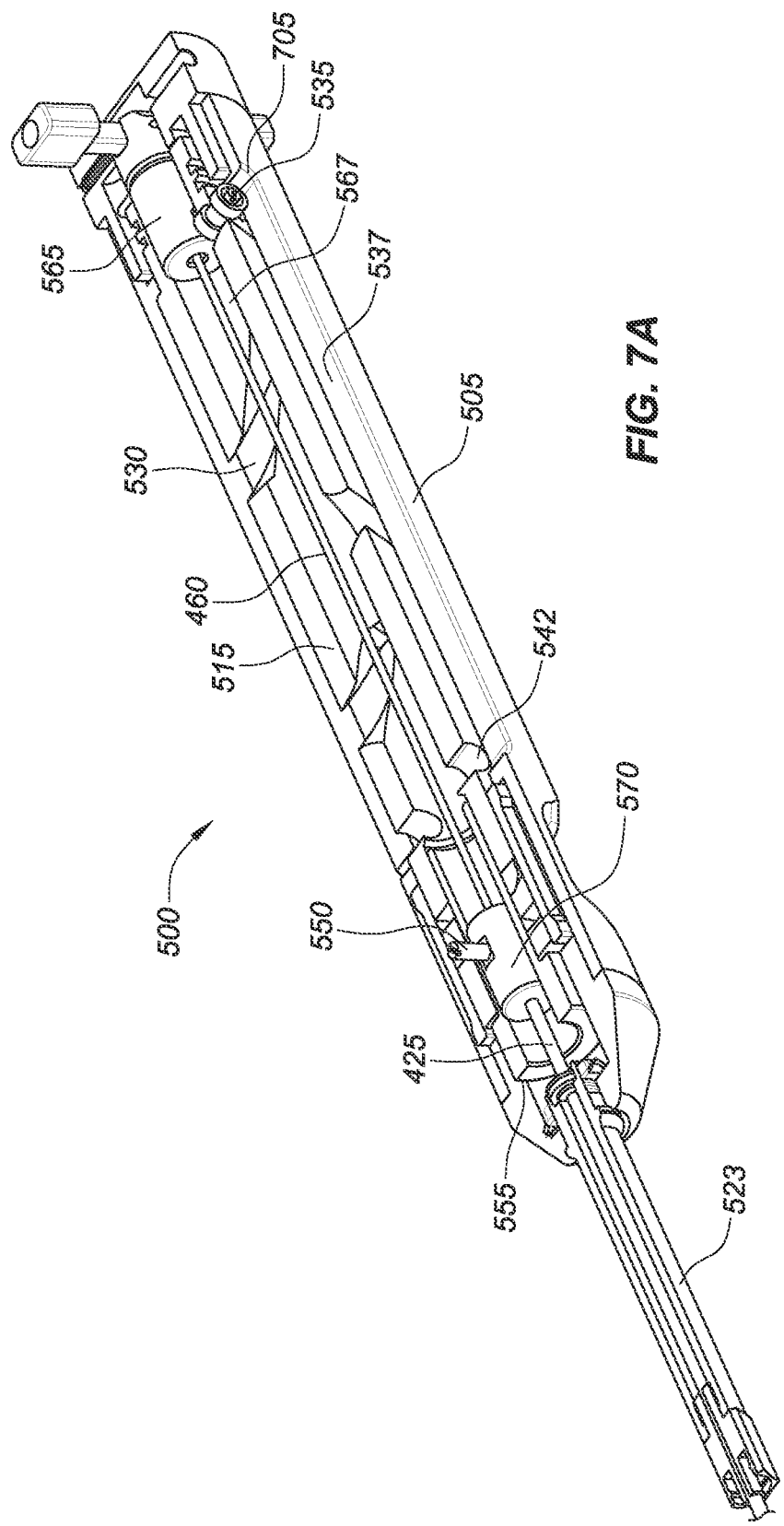
FIGS. 7A-7B, 8A-8B, and 9 are perspective views depicting a delivery device in accordance with some example embodiments of the present disclosure.

FIG. 7A illustrates a cut-away view of camming barrel 515 to show internal components of delivery device 500 in accordance with some embodiments of the disclosure. As shown, delivery device 500 can include a shaft 460, anti-rotation sleeve 555 (cut-away view), a shaft-driver body 565, and a sheath-driver body 570. Shaft-driver body 565 is disposed within a lumen 567 of camming barrel 515. Shaft-driver body 565 can be sized to slidably fit into lumen 567 and to secure shaft 460 along the longitudinal axis of camming barrel 515. Shaft 460 is rigidly coupled to shaft-driver body 565 such that when shaft-driver body 565 is translated and/or rotated within lumen 567, shaft 460 will experience corresponding translations and rotations. Shaft-driver body 565 is also securely attached to cam follower 535, thus when cam follower 535 moves within groove 530, shaft-driver body 565 will rotate and translate as dictated by groove 530. As previously mentioned, slot 537 on main body 505 is designed to constrain cam follower 535 such that cam follower 535 can only move back and forth along the longitudinal axis of camming barrel 515.

Delivery device 500 can also include a sheath-driver body 570 that is securely attached to sheath 425 and cam follower 550. Sheath-driver body 570 includes a lumen to receive sheath 425 at an end close to the distal end of camming barrel 515. The lumen of sheath-driver body 570 can also receive and pass-through shaft 460 into sheath 425. Sheath-driver body 570 can be sized to slidably fit into the lumen of an anti-rotation sleeve 555, which is also appropriately sized to slidably hold sheath-driver body 570 such that the longitudinal axis of the sheath-driver body is along the longitudinal axis of camming barrel 515. In this way, when shaft 460 is translated toward the distal end of camming barrel 515, shaft 460 can be easily pass-through sheath-driver body 570 and into sheath 425 (see also FIG. 7B).

Figure 7B:
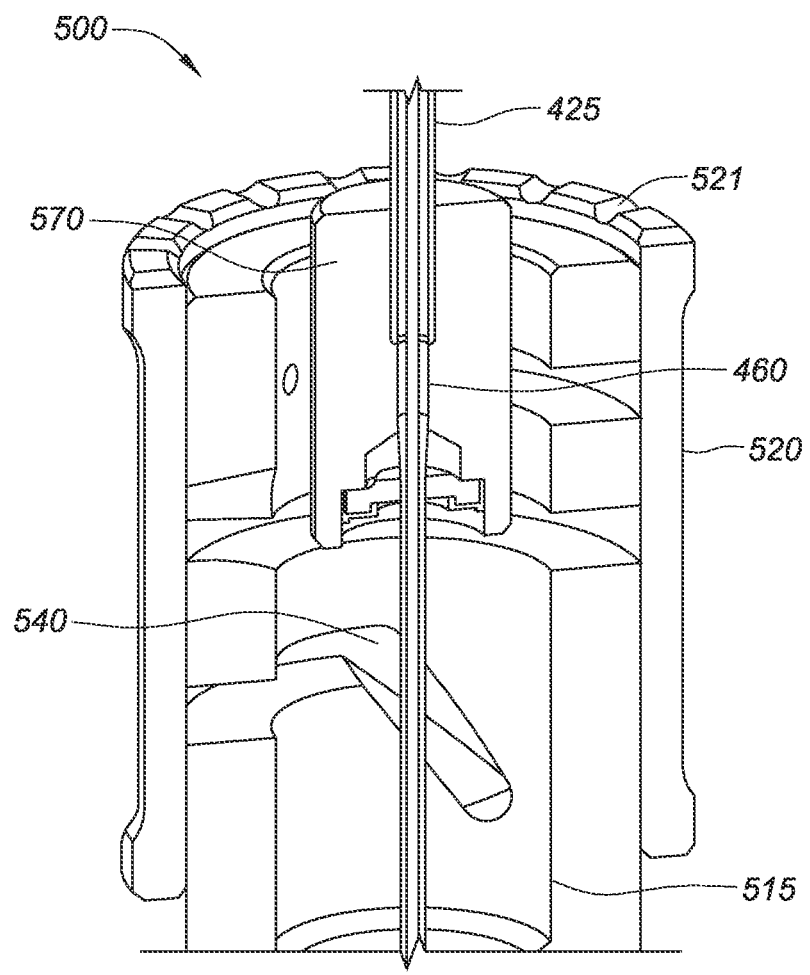

FIG. 7B is a cut-out view depicting a portion of delivery device 100 where knob 520 is located, but without anti-rotation sleeve 555. As shown, sheath 425 terminates within sheath-driver body 570. However, sheath 425 has an opening at the termination end to allow shaft 460 to pass through.

When camming barrel 515 rotates, groove 540 moves under cam follower 550 and forces cam follower 550 to translate within the slot of anti-rotation sleeve 555. The translation of cam follower 550 also causes sheath-driver body 570 to move proximally (toward shaft-driver body 565). The translation of sheath-driver body in the proximal direction causes sheath 425 to retract. Anti-rotation sleeve 555 can be rigidly affixed to main body 505 using a pin and/or adhesive, or by using an anti-rotation mechanical feature on the inner lumen of main body 505.

As shown in FIG. 7A, cam followers 535 and 550 are in their initial undeployed position. Once camming barrel 515 is rotated by rotating knob 520 (not shown, see FIG. 5), cam follower 535 will traverse along groove 530 toward penultimate position 542 and subsequently to end position 543 (not shown, see FIG. 6A). In another perspective, as camming barrel 515 rotates, groove 530 moves under cam follower 535, which is only allowed to move in the axial direction due to the constraint provided by slot 537. As shown in FIG. 7A, slot 537 runs along main body 505, and parallel to the longitudinal axis of camming barrel 515, from a starting position 705 to end position 543. While cam follower 535 moves toward end position 543, cam follower 550 moves within groove 540 and slot 650 (not shown, see FIG. 10A) of anti-rotation sleeve 555 (see also FIGS. 6 and 10A) from starting position 541 to penultimate position 544a and subsequently to end position 544b (see also FIG. 6A).

Figure 8A:
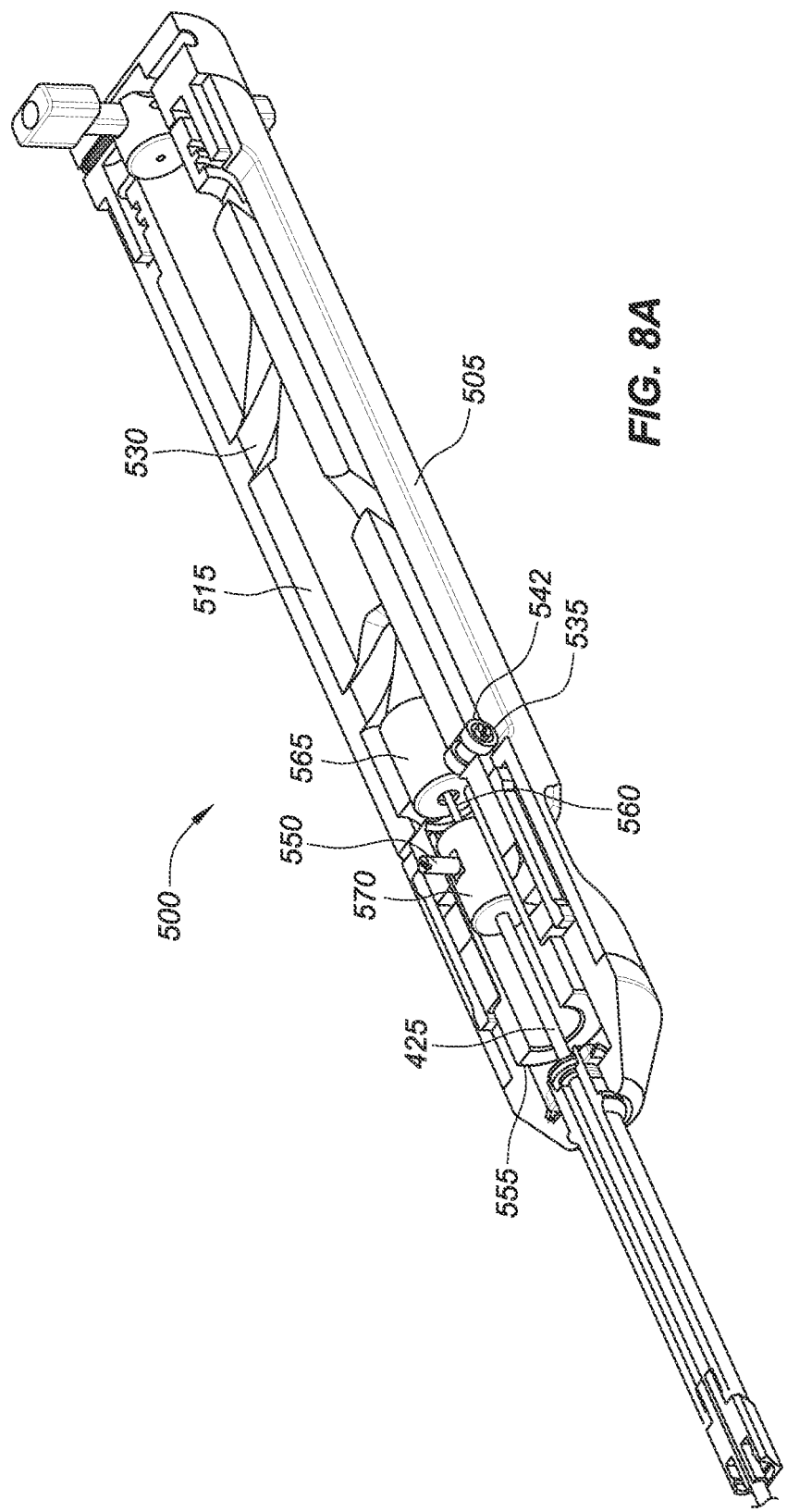
Figure 8B:
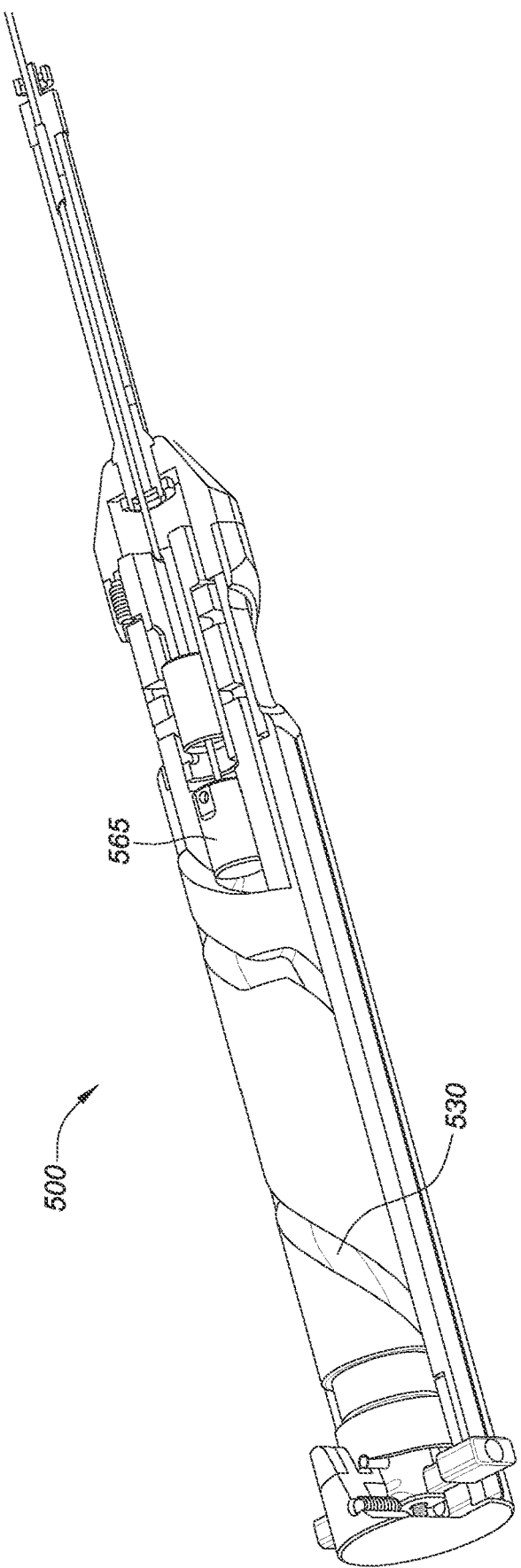

FIG. 8A illustrates a cutout view of delivery device 500 near the end of the rotation/deployment procedure. FIG. 8B illustrates a partial cutout view of delivery device 500 near the end of the rotation/deployment procedure. Once camming barrel 515 is rotated until cam follower 535 reaches the end of groove 530 (at position 543), shaft-driver body 565 is located near the distal end of camming barrel 515 and is closer to sheath-driver body 570, which has moved toward the proximal end of camming barrel 515 (closer to shaft-driver body 565).

Figure 9:
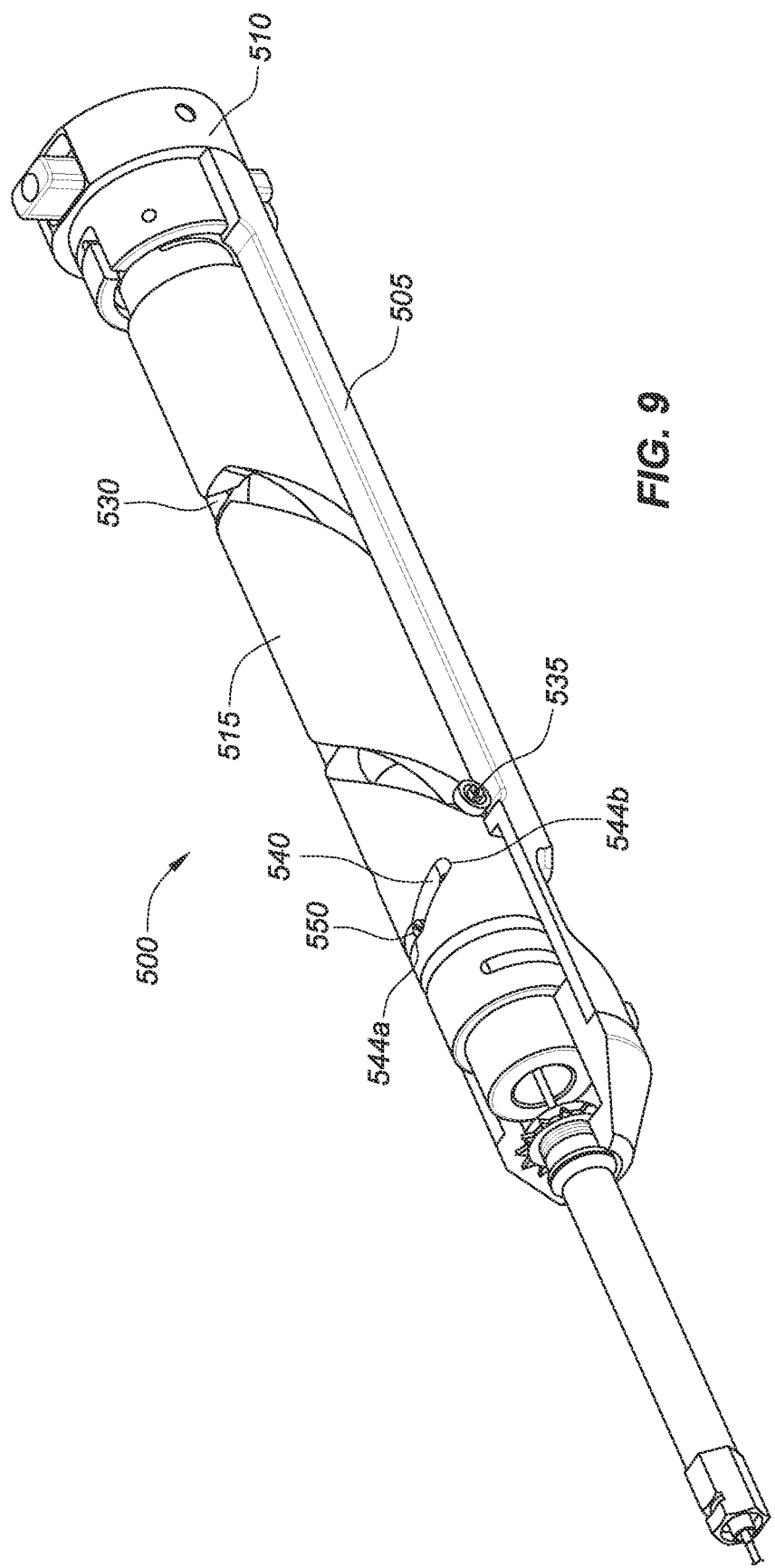

FIG. 9 is a perspective view of delivery device 500 near the end of the rotation/deployment procedure with main body 505 in a cut-away view. As shown, cam follower 550 is at its penultimate position 544a. Cam follower 550 is prevented to move to end position 544b until end cap 510 is actuated to allow camming barrel 515 to be further rotated. End cap 510 also serves as an actuatable barrel portion, when actuated, actuatable barrel 510 either prevents or enables camming barrel 515 to further rotate after cam follower 550 has reached position 544a. More discussion of the actuatable barrel and its related components will be provided below.

As cam follower 550 moves toward the proximal end of camming barrel 515, cam follower 550 also causes sheath-driver body to proximally translate and thereby pulling the rigidly attached sheath 425 (not shown, FIG. 7A) toward the proximal end of camming barrel 515. When sheath 425 is pulled back into the body of camming barrel 515, a portion of implantable device 100 (e.g., connecting member 110a) is exposed at the end of sheath 425. However, as mentioned, once cam follower 535 reaches penultimate position 544a, camming barrel 515 is locked and cam follower 550 cannot move to end position 544b of groove 540 until actuatable barrel 510 is actuated to release camming barrel 515 and allow it to be further rotated. This final movement of cam follower 550 between penultimate position 544a to position 544b causes sheath 425 to further retract into the lumen of camming barrel 515 and thereby expose grasping portion 450 (see FIGS. 4F-H) of shaft 460. Once grasping portion 450 is exposed, implantable device 100 is freed and releases from delivery device 500.

Figure 10D:
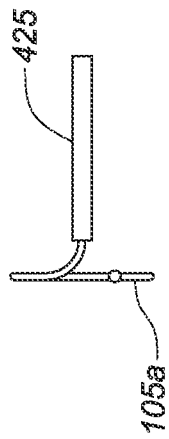
Figure 10F:
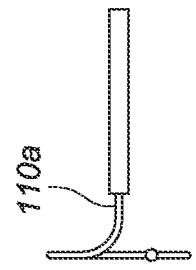
Figure 10A:
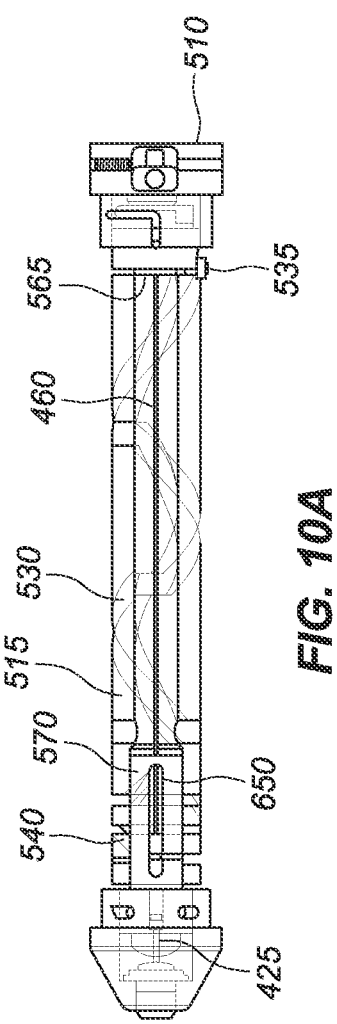
Figure 10C:
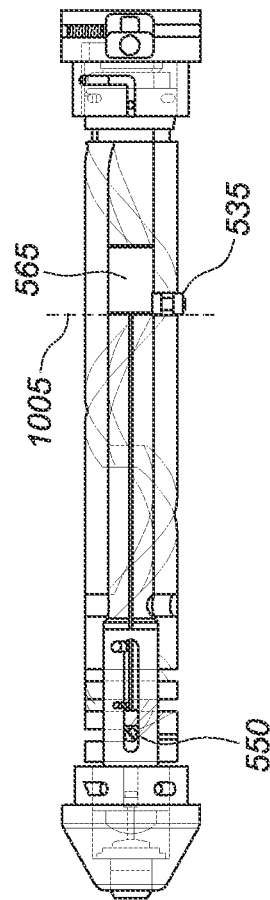
Figure 10E:
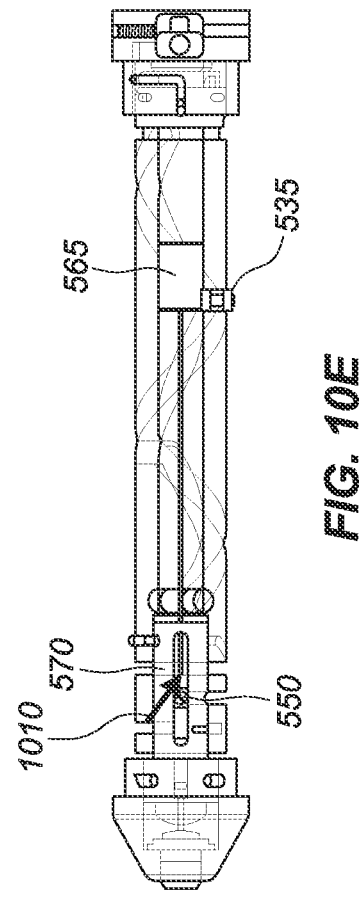
Figure 10H:
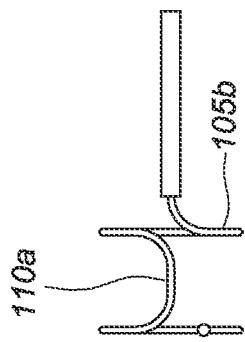
Figure 10J:
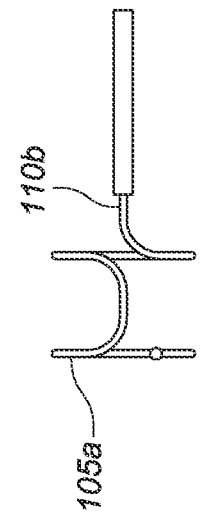
Figure 10G:
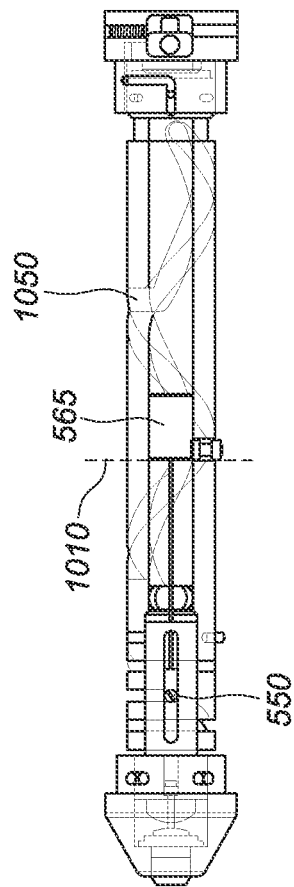
Figure 10I:
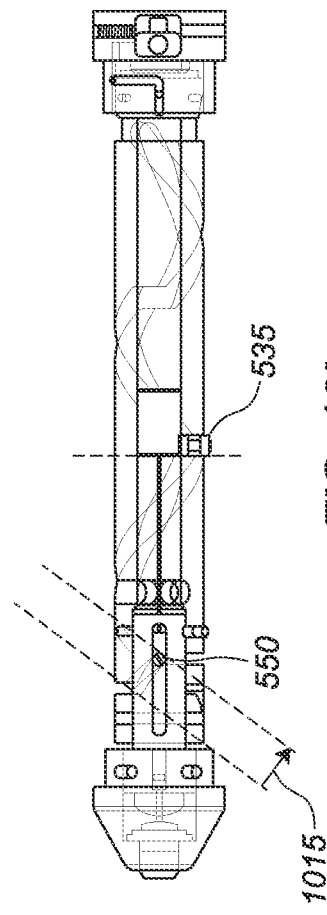
Figure 10L:
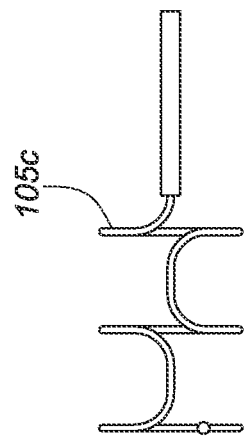
Figure 10N:
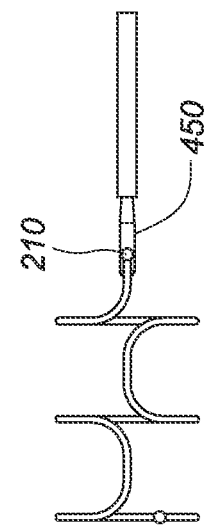

FIGS. 10A-10N depict the positions and movements of various components of delivery device 500 during the deployment process in accordance with some embodiments of the present disclosure. The start of the deployment process for implantable device 100 is illustrated by FIG. 10A where cam follower 535 and shaft-driver body 565 are at the starting/default position. At the distal end of camming barrel 515, sheath-driver body 570 is near the distal end of camming barrel 515. Shaft-driver body 565 and sheath-driver body 570 are farthest away from each other at this stage. Extending out of the end of adapter shaft 523 (see FIG. 5A) is sheath 425, which extends from sheath-driver body 570 within the lumen of camming barrel 515 to beyond the exit opening of adapter shaft 523. FIG. 10B illustrates sheath 425 in the initial configuration—before deployment of implantable device 100. Here, implantable device 100 is completely embedded within sheath 425.

FIG. 10C illustrates the first stage of deployment where ring member 105a is spiraled or spun out of sheath 425 (see FIG. 10D). As shown in FIG. 10C, shaft-driver body 525 and cam follower 535 have moved to a new position at 1005. This is caused by the rotation of camming body 515, which can be done by rotating knob 520 (not shown, see FIG. 5A). When camming barrel 515 is rotated, cam follower 535 traverses along groove 530 and thereby causes shaft-driver body 565 to correspondingly rotate and translate. The rotation and translation of shaft-driver body 565 also causes shaft 460 to rotate and translate, which in turn causes ring member 105a of implantable device 100 to rotate and translate out of sheath 425 (FIG. 10D). The rotation of camming barrel 515 also causes cam follower 550 to simultaneously move within groove 540 at the distal end of camming barrel 515.

Between the positions of FIG. 10C and FIG. 10E, cam follower 535 moves within a radial portion of groove 530. During the traversal of the radial portion, shaft-driver body 565 rides in the radial portion of groove 530 to maintain its axial position (i.e., without any axial translation). At the same time, cam follower 550 moves within a helical portion of groove 530 toward the proximal end of camming barrel 515. This causes cam follower 550 to push sheath-driver body toward the proximal end of delivery device 500 and in turn retract sheath 425 into the body of camming barrel 515. FIG. 10F illustrates the exposure of connecting member 110a as sheath 425 is being proximally retracted.

FIG. 10G illustrates second ring member 105b being pushed out of sheath 425 (see FIG. 10H). As shown in FIG. 10G, shaft-driver body 565 and cam follower 535 have moved to a new position 1010. During the transition between positions 1005 and 1010, second ring member 105b is deployed into the patient's urethra as depicted in FIG. 10H. While cam follower 535 is traversing between positions 1005 and 1010, cam follower 550 simultaneously traverses a radial slot of groove 540. This movement has zero axial component, which thereby causes sheath-driver body 570 to remain proximally stationary.

Between FIGS. 10G and 10I, cam follower 535 traverses a radial slot portion (blocked from view by cam follower 535 and shaft-driver body 525). The radial slot portion of groove 530 (that is blocked from view) is similar to radial slot 1050, which is the radial slot of a previous radial transition between FIGS. 10C and 10E. At the same time, cam follower 550 traverses a helical slot of groove 540 as shown by arrow 1015. This movement has an axial component and thus causes sheath-driver body 570 to retract in the proximal direction (toward shaft-driver body 525). The additional retraction of sheath 425 further exposes connecting member 110b of implantable device 100 (see FIG. 10J).

Figure 10K:
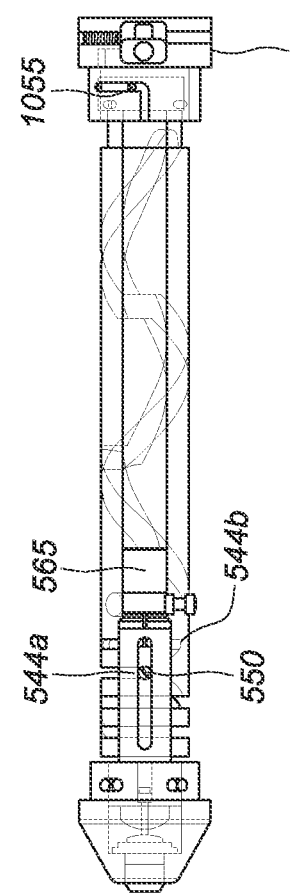

Between FIGS. 10I and 10K, third ring member 105c is pushed out as cam follower 535 traverses the last helical portion of groove 530. FIG. 10L illustrates ring member 105c in the deployed position.

Figure 10M:
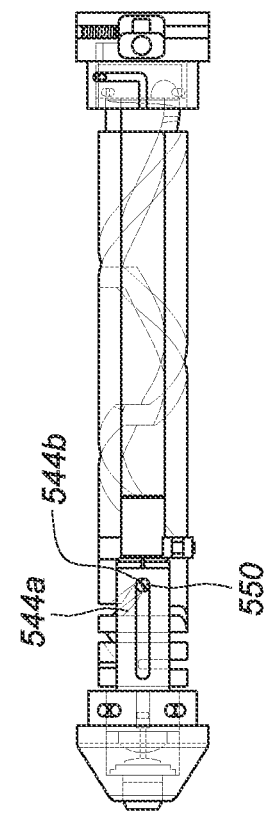

FIGS. 10K and 10M illustrate the last stage of deployment of implantable device 100. During this stage, cam follower 535 traverses a radial slot of groove 530 from penultimate position 542 to end position 543 (not shown, see FIG. 6A). At the same time, cam follower 550 traverses a helical slot of groove 540 from penultimate position 544a to end position 544b. In an initial setting of delivery device 500, both cam followers 535 and 570 are prevented to traverse from their respective penultimate position to the end position as camming barrel 515 is locked by a locking mechanism located at the proximal end of camming barrel 515.

In some embodiments, delivery device 500 does not include groove 530, and only helical groove 540 is present. In this embodiment, implantable device 100 does not need to be spun (or pushed) out of sheath 425. Instead, the deployment procedure involves only retracting sheath 425 to slowly expose implantable device 100 contained within sheath 425 (which is partially shown in FIG. 10N).

Figure 11:
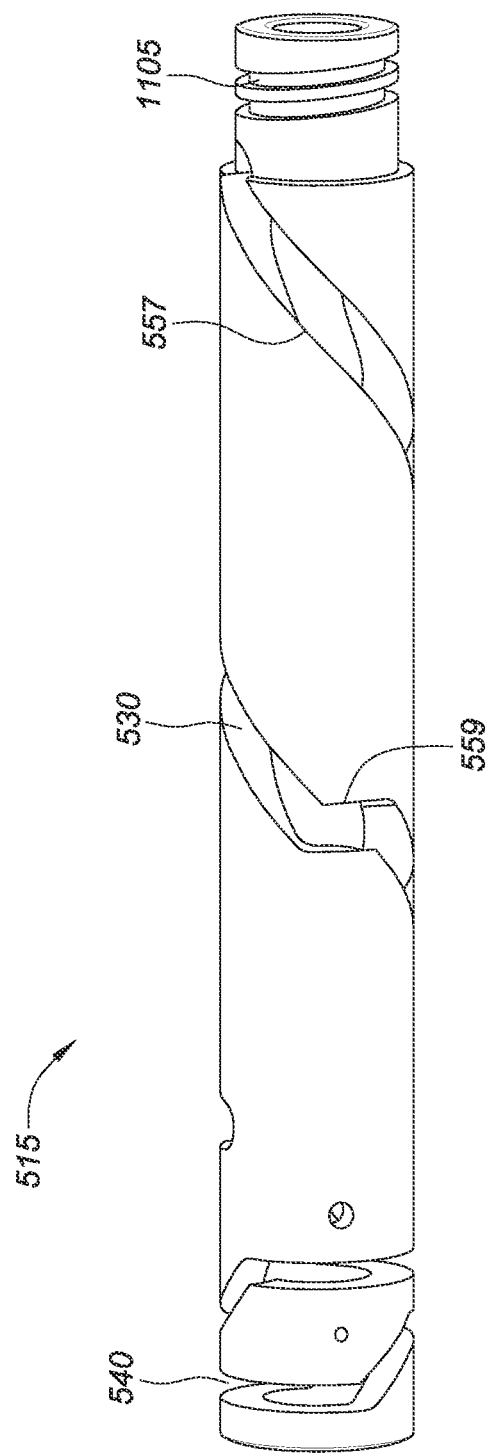
FIG. 11 is a perspective view depicting a camming barrel in accordance with some example embodiments of the present disclosure.
Figure 12A:
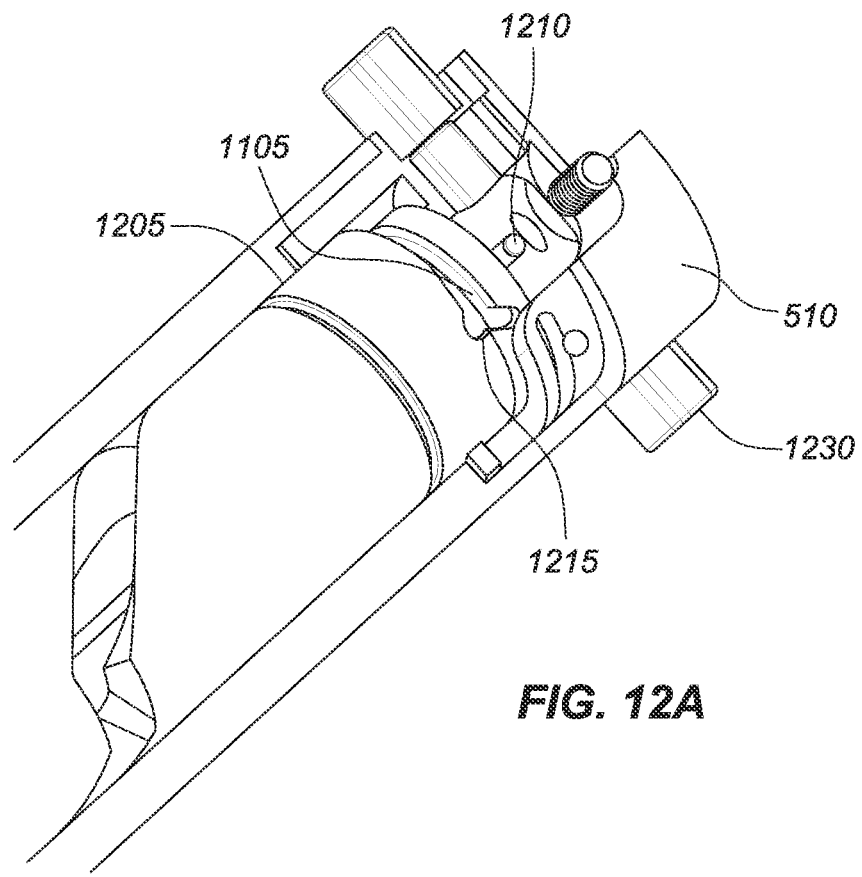
FIGS. 12A-12I are perspective views depicting a locking mechanism of the delivery device in accordance with some example embodiments of the present disclosure.
Figure 12B:
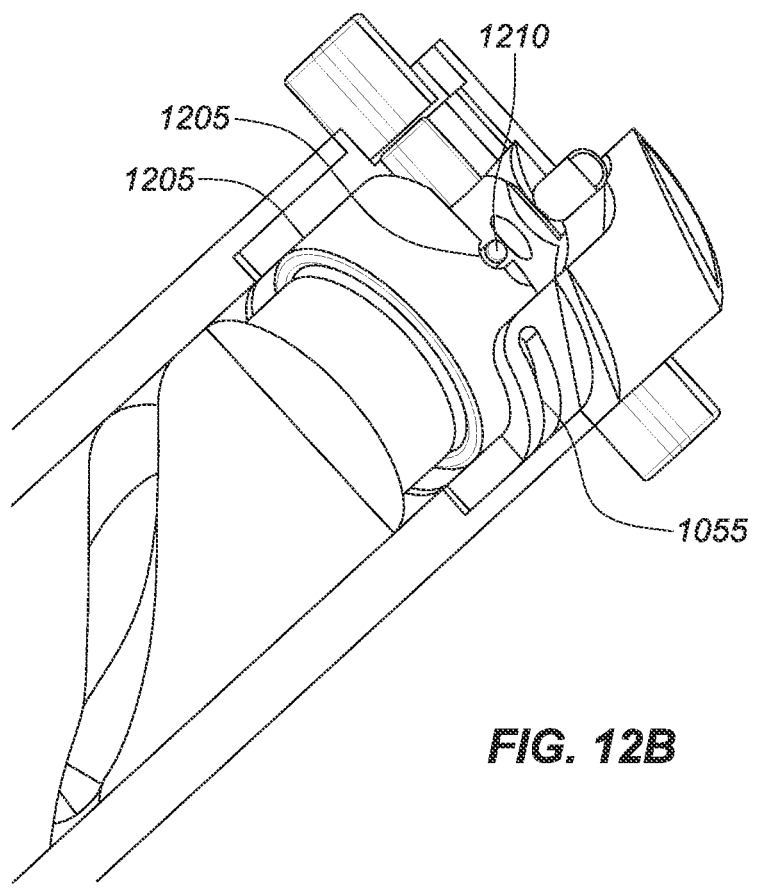
Figure 12C:
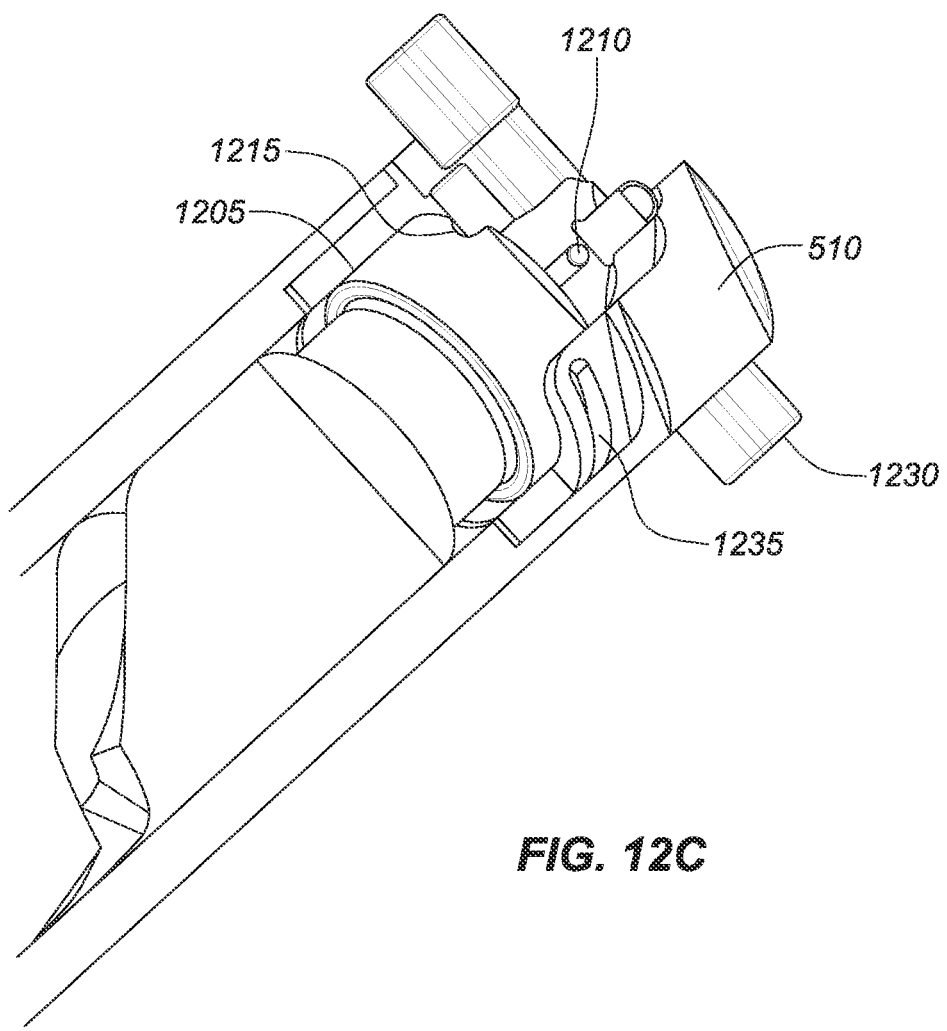
Figure 13:
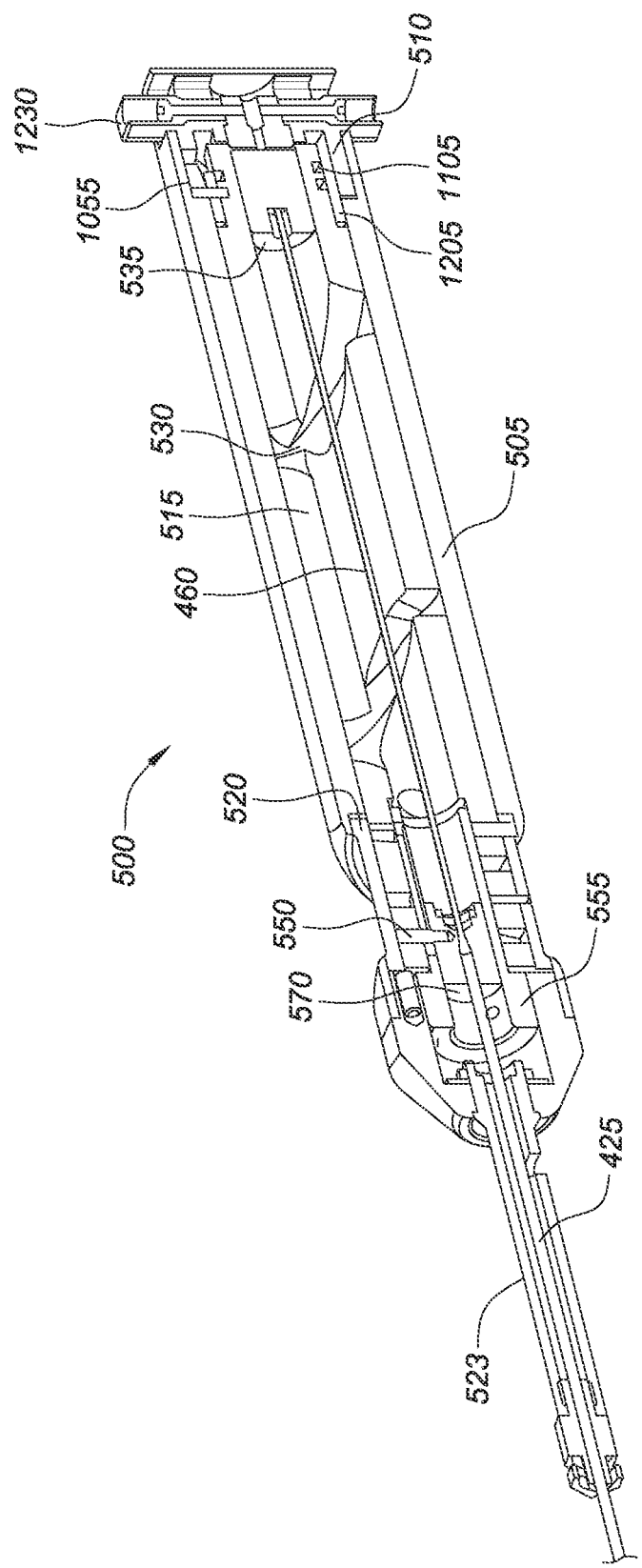
FIGS. 13 and 14 are perspective views depicting example embodiments of the delivery device.

FIGS. 10K, 11, 12A-C, and 13 will be described together to further illustrate the locking mechanism. FIG. 11 depicts camming barrel 515 in accordance with some embodiments of the present disclosure. FIGS. 12A and 12B depict various internal components of the locking mechanism, and FIG. 13 depicts a cross-section of delivery device 500 in accordance with some embodiments of the present disclosure. The locking mechanism includes a third groove 1105 (see FIG. 11) at the proximal end of camming barrel 515, end cap 510, a cam follower 1055 (see FIG. 10K), and a locking sleeve 1205 (see FIG. 12A). As shown in FIG. 11, camming barrel 515 includes groove 1105, which drives cam follower 1055 along locking sleeve 1205 as camming barrel 515 is being rotated by knob 520. Upon deployment of implantable device 100 or the clockwise rotation of camming barrel 515, locking sleeve 1205 moves toward the proximal end of camming barrel 515. Once cam followers 535 and 550 reach their respective penultimate position, notch 1215 of locking sleeve 1205 engages pin 1210 (see FIG. 12B), which is rigidly attached to actuatable end cap 510. This can prevent the accidental deployment of implantable device 100. Once camming barrel 515 is allowed to further rotate, cam follower 550 will move to end position 544b. This will cause sheath 425 to retract and expose grasping portion 450 of shaft 460. The exposure of the grasping portion will free end member 210 of implantable device 100 from the confines of sheath 425 (see FIG. 10N). This effectively ends the deployment procedure as implantable device 100 is released from grasping portion 450.

Figure 12D:
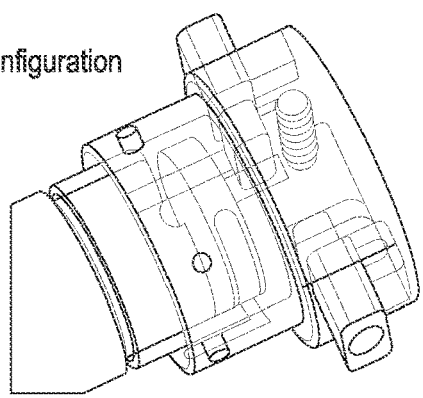
Figure 12G:
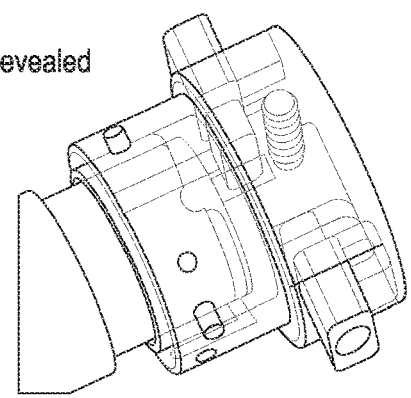
Figure 12E:
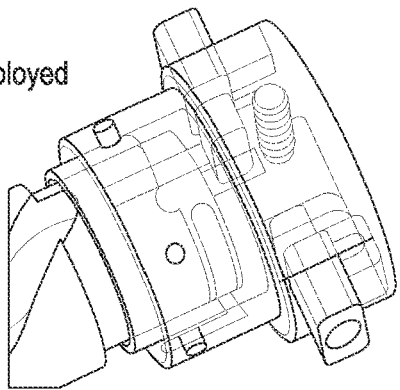
Figure 12H:
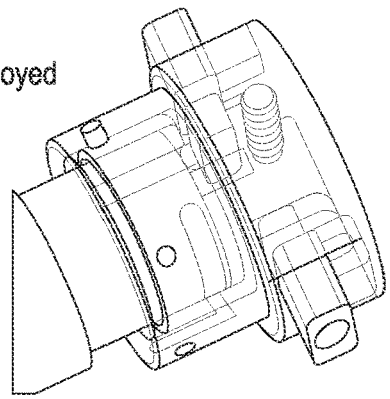
Figure 12F:
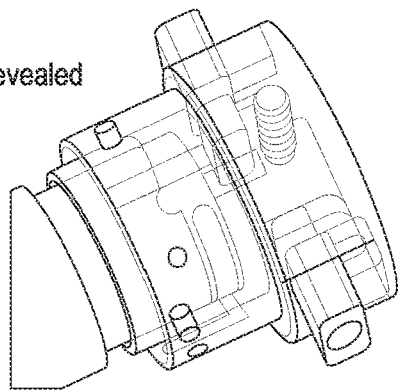
Figure 12I:
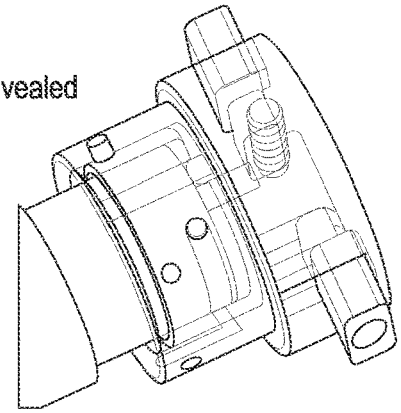

FIGS. 12D-12I are perspective and semi-transparent views of the locking mechanism during the deployment progression of implantable device 100. FIGS. 12D, 12E, and 12F correspond with the deployment progression as depicted in FIGS. 10A, 10B, and 10C, respectively. FIGS. 12G, 12H, and 12I correspond with the deployment progression as depicted in FIGS. 10A, 10B, and 10C, respectively. FIGS. 12H and 12I also correspond with the deployment progression as depicted in FIGS. 12B and 12C, respectively.

Figure 12J:
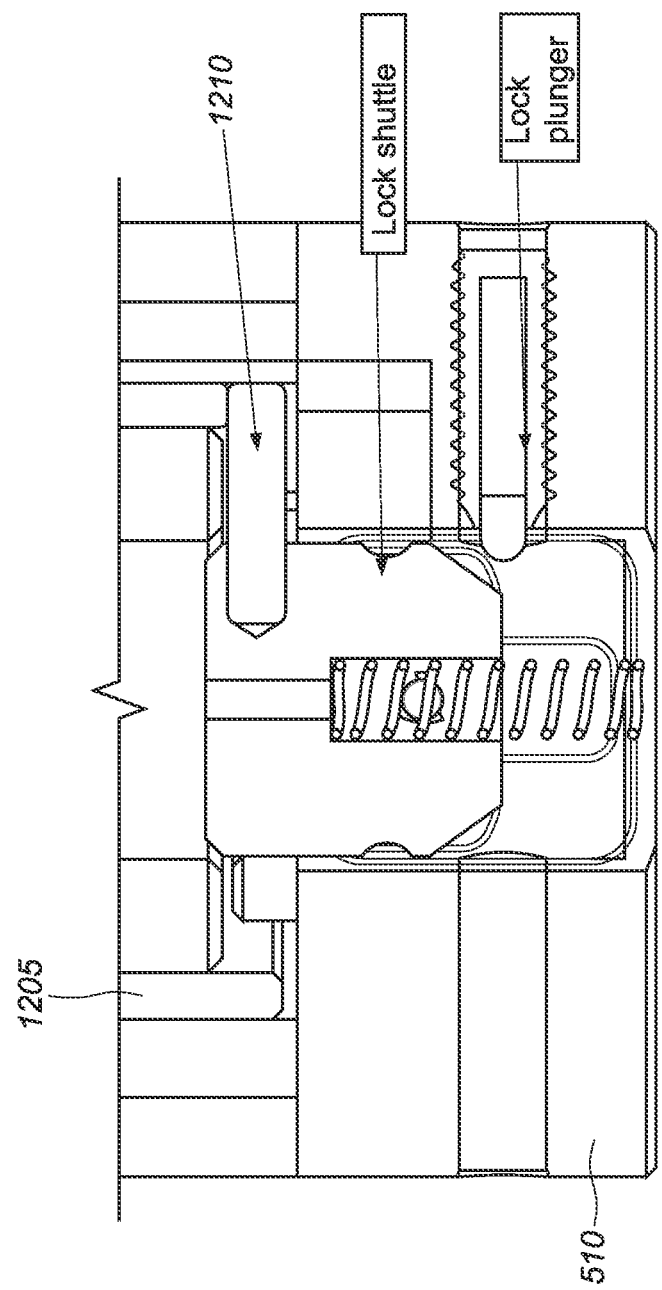
FIG. 12J is a cross-sectional view depicting a locking mechanism of the delivery device in accordance with some example embodiments of the present disclosure.

FIG. 12J is a cut-away view of the locking mechanism in accordance with some embodiments of the present disclosure. In some embodiments, end cap 510 is actuatable because pin 1235 can be moved along the longitudinal axis of camming barrel 515. In the initial setting (also a default setting), pin 1235 is biased toward the distal end of camming barrel 515 (see FIGS. 12A and 12B). During deployment, cam follower 1055 moves proximally via the helical path 1105, until it reaches the penultimate lock position. The L-shaped slot of end cap 510 is designed to axially receive pin 12354 and locking sleeve 1205. The longer the axial length of the slot of end cap 510, the further camming barrel 515 can rotate before notch 1215 of locking sleeve engages pin 1210.

FIG. 12B illustrates the position of sleeve 1205 and notch 1215 with respect to pin 1210 when cam followers 535 and 550 are at their penultimate positions. As shown, pin 1210 engages notch 1215 which prevents camming barrel 515 from further rotation because cam follower 1055 is rigidly affixed to sleeve 1205. Again, this can prevent the accidental release of implantable device 100 until end cap 510 is actuated by pushing (or pulling) the end cap handle 1230 toward the proximal direction.

FIG. 12C illustrates when end cap 510 is actuated and final rotation (release) is completed. As shown, pin 1210 is pulled by the user toward the proximal end of end cap 510. Since pin 1210 is no longer preventing cam rotation, camming barrel 515 may further rotate (clockwise), which moves cam follower 1055 to the radial end of the L-shaped slot of end cap 510. In many embodiments, this ends the implantable device deployment procedure.

Figure 14:
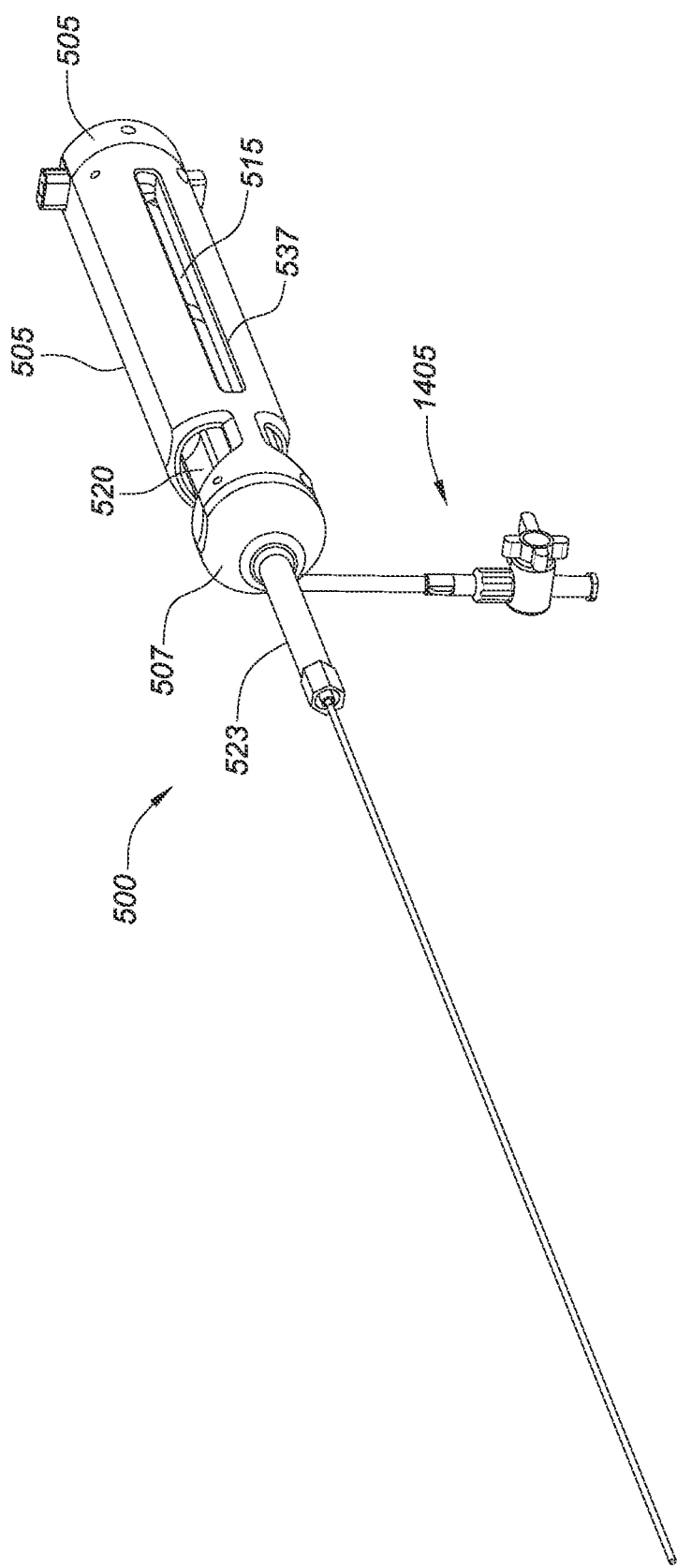

FIG. 14 illustrates a perspective view of a fully assembled delivery device 500 in accordance with some embodiments of the present disclosure. As shown, delivery device 500 includes a drainage assembly 1405 for draining fluid within the urethra during the deployment of implantable device 100. Assembly 1405 can also be used to flush or add fluid during the procedure.

Figure 15:
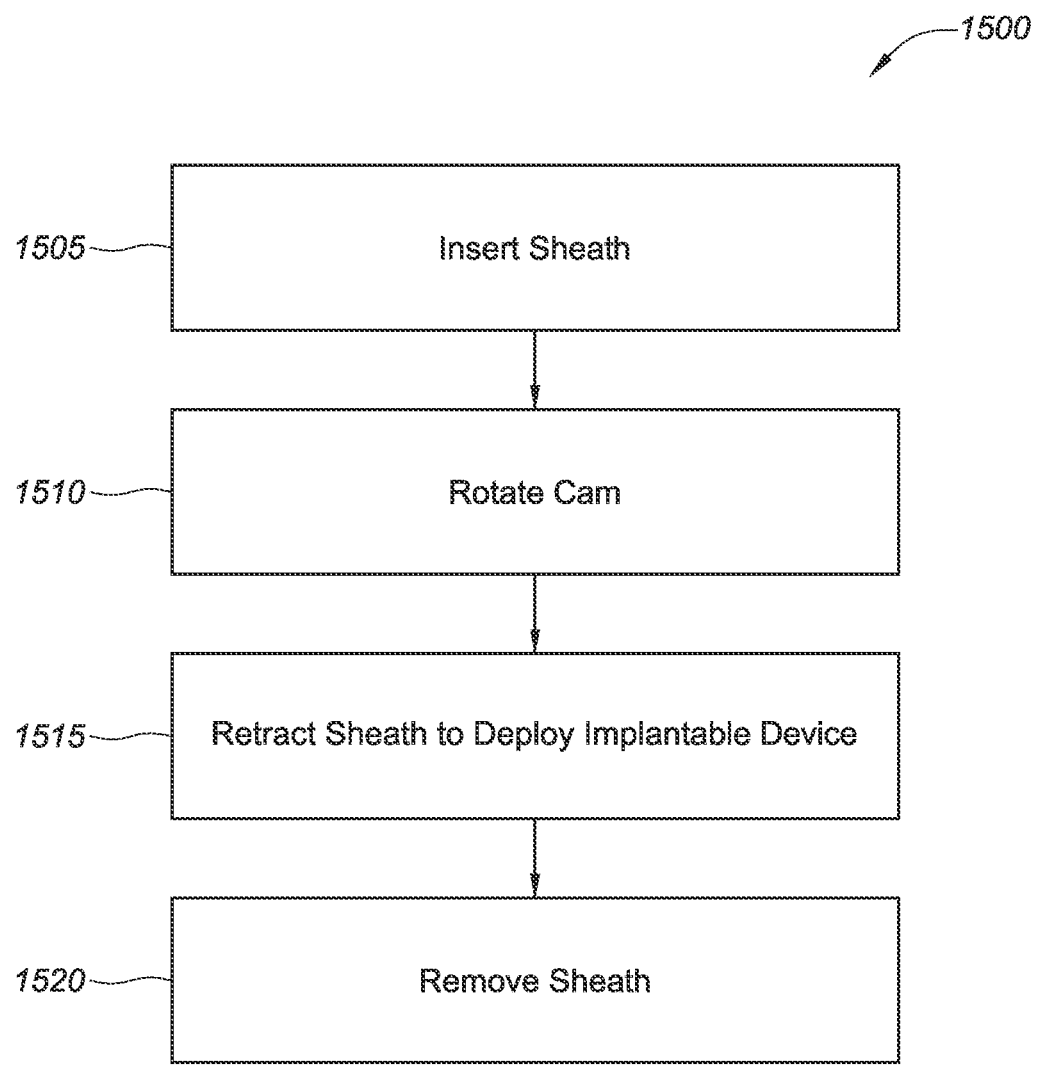
FIGS. 15 and 16 are block diagrams depicting the deployment process of an implantable device in accordance with some example embodiments of the present disclosure.

FIG. 15 illustrates a process 1500 for deploying an implantable device (e.g., implantable device 100) in accordance with some embodiments of the present disclosure. Process 1500 can start at 1505 where a sheath (e.g., sheath 425) containing the implantable device 100 is inserted into a patient's urethra. At 1510, to deploy the implantable device, the cam of the delivery device (e.g., delivery device 500) is rotated. This can be done by turning a knob (e.g., knob 520) of the delivery device 500, for example. Alternatively, the camming barrel (e.g., camming barrel 515) of the delivery device 500 may be directly rotated. At 1515, sheath 425 is driven backward, which causes sheath 425 to retract into the body of delivery device 500. As sheath 425 is slowly being retracted, implantable device 100 is slowly exposed and deployed within the urethra. Once implantable device 100 is fully deployed and released, sheath 425 is removed from the patient's body at 1520.

Figure 16:
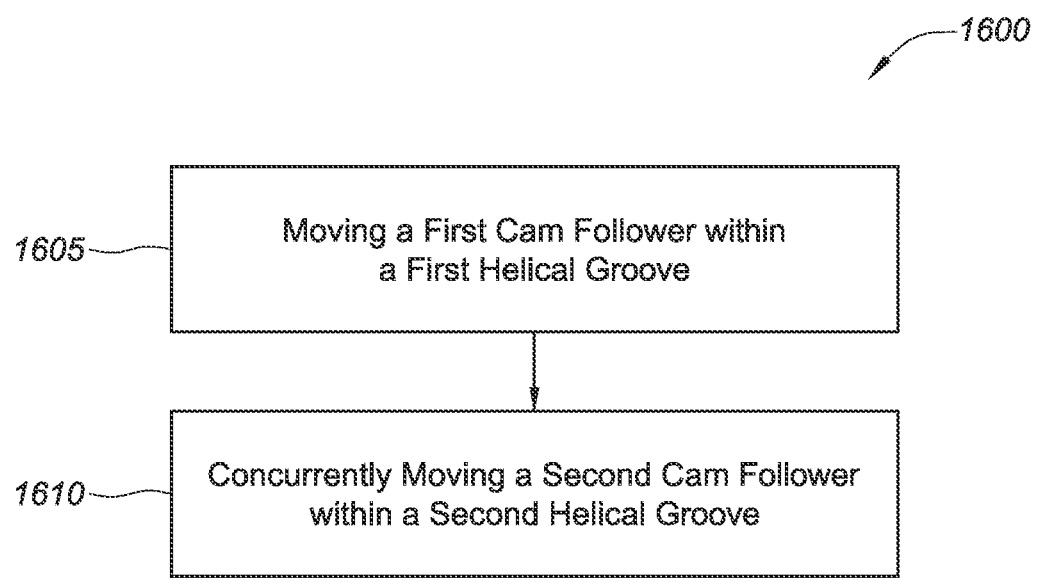

FIG. 16 illustrates a process 1600 for retracting sheath 425 and for spiraling out implantable device 100 in accordance with some embodiments of the present disclosure. Process 1600 starts at 1605 where a first cam follower (e.g., cam follower 535 or 550) is moved (rotated and/or translated) within a first groove (e.g., groove 530 or 540). In some embodiments, the first cam follower is constrained to only move in the axial direction. This can be accomplished using a slot disposed parallel to the longitudinal axis of the main body of the delivery device (e.g., main body 505 or camming barrel 515). An anti-rotation sleeve with a longitudinal slot may also be employed to restrict the movement of the cam follower. At 1610, when the first cam follower (e.g., cam follower 535) is being moved within the first groove, the second cam follower (e.g., cam follower 550) is also concurrently moved within the second groove. In some embodiments, while the first cam follower is moving within a helical slot portion of the first groove, the second cam follower is concurrently moving within a radial slot portion of the second groove. Additionally, while the first cam follower is moving within a radial slot portion of the first groove, the second cam follower is concurrently moving within a helical slot portion of the second groove. In this way, the movements of both cam followers 535 and 550 are not the same at any point of time. This also enables two main types of coordinated movement. The first type is when the first cam follower pushes shaft 425 in the distal direction while the second cam follower holds sheath 425 axially stationary. The second type is when the first cam follower holds shaft 425 axially stationary while the second cam follower retracts sheath 425 in the proximal direction.

In certain situations, it may be desirable to return implantable device 100 to its housed position within sheath 425 prior to device 100 being fully released from grasper 450. For example, if the medical professional views the partially deployed location or position of implantable device 100 as not optimal or otherwise desirable, then implantable device 100 can be partially or fully retracted into sheath 425 (or sheath 425 can be advanced over device 100, or a combination of both movements) by performing one or more steps of the deployment procedures as described herein (e.g., with respect to FIGS. 4A-4E and 10A-10N) in reverse order. For example, each deployment step executed to expose a portion of device 100 (e.g., a portion of a first ring 105, a first ring 105 and a portion of a connecting member 110, multiple rings 105 and an intervening connection member 110, and so forth) from the open distal end of sheath 425 can be performed in reverse, with the overall sequence of executed steps also being performed in reverse. For example, if the delivery embodiment is configured such that rotation of camming barrel 515 (or knob 520) in a first (e.g., counterclockwise) direction causes a portion of implantable device 100 to exit the open distal end of sheath 425, then rotation of camming barrel 515 (or know 520) in a second opposite (e.g., clockwise) direction causes the exposed portion of implantable device 100 to return to the housed position within sheath 425 and thereby recover implantable device 100. Delivery device 500 can then be repositioned (e.g., without removing from the body) and the delivery procedure can be started anew. This process can be repeated until an optimal or desirable placement is achieved, at which point implantable device 100 can be fully released and separated from delivery device 500.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

In many instances, entities are described herein as being coupled to other entities. It should be understood that the terms "coupled" and "connected" (or any of their forms) are used interchangeably herein and, in both cases, are generic to the direct coupling of two entities (without any non-negligible intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

As used herein and in the appended claims, the singular forms "a," "an," and "the" include plural referents unless the context clearly dictates otherwise.

The examples and embodiments provided herein are provided for illustrative purposes and are not intended to limit the application or claims provided herein. It will be understood that the specific embodiments disclosed herein and the systems, components, methods, etc. described herein need not take the specific form described, but can instead be applied in various different or additional manners consistent with the present disclosure and claims. It will further be understood that the present disclosure need not take the specific form explicitly described herein, and the present disclosure is intended to include changes variations thereof, consistent with the appended claims and the present disclosure, for example, to optimize the subject matter described herein. The disclosed subject matter is not limited to any single or specific embodiment described herein, but rather should be construed in breadth and scope in accordance with the appended claims.

The invention claimed is:

1. An apparatus for delivering an implantable device, the apparatus comprising:
    a camming barrel having a first groove at the distal end of the camming barrel;
    a sheath, partially located within a lumen of the camming barrel, the sheath having a distal region for storing the implantable device;
    a first cam follower coupled to the sheath, wherein the first cam follower is configured to travel within the first groove of the camming barrel and to rotate and translate the sheath, wherein translation of the sheath causes the sheath to retract into the camming barrel; and
    a sheath-driver body slidably located within the camming barrel, wherein the sheath-driver body is rigidly coupled to the sheath and to the first cam follower, wherein the sheath-driver body is configured to secure the sheath along the longitudinal axis of the camming barrel.

2. The apparatus of claim 1, wherein the sheath-driver body is sized to fit within the lumen of the camming barrel and to hold sheath-driver body along the longitudinal axis of the lumen.

3. The apparatus of claim 1, wherein the sheath-driver body comprises a cylindrical or spherical body.

4. The apparatus of claim 1, further comprising:
a shaft located along the longitudinal axis of the lumen of the camming barrel and coupled to the implantable device, wherein the sheath is configured to receive and pass through the shaft;
a second groove at a proximal end of the camming barrel; and
a second cam follower coupled to the shaft, wherein the second cam follower is configured to travel within the second groove of the camming barrel and to rotate and translate the shaft, wherein the rotation and translation of the shaft causes corresponding rotation and translation of the implantable device.

5. The apparatus of claim 4, wherein each of the first and second grooves comprises a plurality of linked sloped and radial slots.

6. The apparatus of claim 5, wherein the first and second grooves are arranged on the camming barrel such that when the first cam follower is traversing a radial slot at a first time, the second cam follower is traversing a sloped slot, and such that when the first cam follower is traversing a sloped slot at a second time, the second cam follower is traversing a radial slot.

7. The apparatus of claim 1, further comprising a locking mechanism, the locking mechanism comprising:
a locking groove at the proximal end of the camming barrel;
a sleeve having a locking-groove-cam follower, the sleeve disposed over the locking groove such that the locking-groove-cam follower is disposed within the locking groove; and
an actuatable barrel portion disposed over the sleeve, the actual barrel portion having a spring-actuated length selector, when actuated in a locked position, the spring-actuated length selector limits the camming barrel from rotating beyond a predetermined point on the locking groove, wherein the camming barrel is allowed to rotate beyond the predetermined point on the locking groove when the spring-actuated length selector is in an unlocked position.

8. An apparatus for delivering an implantable device, the apparatus comprising:
a camming barrel having a first groove at the distal end of the camming barrel;
a sheath, partially located within a lumen of the camming barrel, the sheath having a distal region for storing the implantable device;
a first cam follower coupled to the sheath, wherein the first cam follower is configured to travel within the first groove of the camming barrel and to rotate and translate the sheath, wherein translation of the sheath causes the sheath to retract into the camming barrel; and
a locking mechanism comprising:
a locking groove at the proximal end of the camming barrel;
a sleeve having a locking-groove-cam follower, the sleeve disposed over the locking groove such that the locking-groove-cam follower is disposed within the locking groove; and
an actuatable barrel portion disposed over the sleeve, the actual barrel portion having a spring-actuated length selector, when actuated in a locked position, the spring-actuated length selector limits the camming barrel from rotating beyond a predetermined point on the locking groove, wherein the camming barrel is allowed to rotate beyond the predetermined point on the locking groove when the spring-actuated length selector is in an unlocked position.

9. The apparatus of claim 8, further comprising:
a sheath-driver body slidably located within the camming barrel, wherein the sheath-driver body is rigidly coupled to the sheath and to the first cam follower, wherein the sheath-driver body is configured to secure the sheath along the longitudinal axis of the camming barrel.

10. The apparatus of claim 9, wherein the sheath-driver body is sized to fit within the lumen of the camming barrel and to hold sheath-driver body along the longitudinal axis of the lumen.

11. The apparatus of claim 9, wherein the sheath-driver body comprises a cylindrical or spherical body.

12. The apparatus of claim 9, further comprising:
a shaft located along the longitudinal axis of the lumen of the camming barrel and coupled to the implantable device, wherein the sheath is configured to receive and pass through the shaft;
a second groove at a proximal end of the camming barrel; and
a second cam follower coupled to the shaft, wherein the second cam follower is configured to travel within the second groove of the camming barrel and to rotate and translate the shaft, wherein the rotation and translation of the shaft causes corresponding rotation and translation of the implantable device.

13. The apparatus of claim 12, wherein each of the first and second grooves comprises a plurality of linked sloped and radial slots.

14. The apparatus of claim 13, wherein the first and second grooves are arranged on the camming barrel such that when the first cam follower is traversing a radial slot at a first time, the second cam follower is traversing a sloped slot, and such that when the first cam follower is traversing a sloped slot at a second time, the second cam follower is traversing a radial slot.

* * * * *